(12) United States Patent
Ito et al.

(10) Patent No.: US 11,890,145 B2
(45) Date of Patent: ***Feb. 6, 2024

(54) ADHESION-PREVENTING COMPOSITION

(71) Applicants: Mochida Pharmaceutical Co., Ltd., Tokyo (JP); The University of Tokyo, Tokyo (JP)

(72) Inventors: Taichi Ito, Tokyo (JP); Seiichi Ohta, Tokyo (JP); Norihiro Kokudo, Tokyo (JP); Mitsuko Isaji, Tokyo (JP); Satoshi Shimizu, Tokyo (JP)

(73) Assignees: The University of Tokyo, Tokyo (JP); Mochida Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/896,474

(22) Filed: Aug. 26, 2022

(65) Prior Publication Data

US 2023/0145308 A1    May 11, 2023

Related U.S. Application Data

(63) Continuation of application No. 16/316,097, filed as application No. PCT/JP2017/025614 on Jul. 13, 2017, now Pat. No. 11,464,597.

(30) Foreign Application Priority Data

Jul. 13, 2016  (JP) ................. 2016-138666

(51) Int. Cl.
| A61B 90/00 | (2016.01) |
| A61L 31/14 | (2006.01) |
| A61L 31/12 | (2006.01) |
| A61L 31/04 | (2006.01) |

(52) U.S. Cl.
CPC .............. *A61B 90/08* (2016.02); *A61L 31/04* (2013.01); *A61L 31/12* (2013.01); *A61L 31/128* (2013.01); *A61L 31/14* (2013.01); *A61L 31/146* (2013.01); *A61B 2090/0816* (2016.02); *A61L 2420/08* (2013.01)

(58) Field of Classification Search
CPC ................. A61L 31/46; A61B 2090/0816
See application file for complete search history.

(56) References Cited

U.S. PATENT DOCUMENTS

| 5,795,584 | A | 8/1998 | Totakura et al. |
| 2002/0190226 | A1 | 12/2002 | Ashby et al. |
| 2004/0137179 | A1 | 7/2004 | Matsuda et al. |
| 2006/0246105 | A1 | 11/2006 | Molz et al. |
| 2007/0009579 | A1 | 1/2007 | Sato |
| 2008/0033392 | A1 | 2/2008 | Gaserod et al. |
| 2008/0254091 | A1 | 10/2008 | Lee et al. |
| 2012/0039959 | A1 | 2/2012 | Tessmar et al. |
| 2012/0107439 | A1 | 5/2012 | Sharma et al. |
| 2015/0320915 | A1 | 11/2015 | Schmidt et al. |
| 2016/0095962 | A1 | 4/2016 | Fukuda et al. |
| 2017/0348465 | A1 | 12/2017 | Saito et al. |
| 2019/0083678 | A1 | 3/2019 | Suzuki et al. |

FOREIGN PATENT DOCUMENTS

| CN | 101257935 A | 9/2008 |
| CN | 102580134 A | 7/2012 |
| CN | 103483625 A | 1/2014 |
| CN | 105339019 A | 2/2016 |
| EP | 0 109 197 A2 | 5/1984 |
| JP | 48-079870 A | 10/1973 |
| JP | 2002-530440 A | 9/2002 |
| JP | 2003-062063 A | 3/2003 |
| JP | 2003-509468 A | 3/2003 |
| JP | 2003-126235 A | 5/2003 |
| JP | 2007-075425 A | 3/2007 |
| JP | 2011-025013 A | 2/2011 |
| JP | 2013-165884 A | 8/2013 |
| JP | 2016-502874 A | 2/2016 |
| WO | WO-93/13136 A1 | 7/1993 |
| WO | WO-00/29449 A1 | 5/2000 |
| WO | WO-01/21196 A1 | 3/2001 |
| WO | WO-2005/026214 A1 | 3/2005 |

(Continued)

OTHER PUBLICATIONS

Alginate-based Biomedical Materials and Clinical Medical Science, edited by Qisheng GU, Shanghai Science and Technology Press, 1st Edition, Apr. 2015, 333-337.

Chaturvedi et al., "Prevention of postsurgical adhesions using an ultrapure alginate-based gel," British Journal of Surgery, 2013, 100(7):904-910.

Gleghorn et al., "Adhesive properties of laminated alginate gels for tissue engineering of layered structures," Journal of Biomedical Materials Research Part A, Jan. 1, 2008, 85A(3):611-618.

International Search Report dated Mar. 27, 2018, in PCT/JP2018/000874.

Kong et al., "Controlling Rigidity and Degradation of Alginate Hydrogels via Molecular Weight Distribution," Biomacromolecules, Sep. 1, 2004, 5(5):1720-1727.

(Continued)

*Primary Examiner* — Gina C Justice
(74) *Attorney, Agent, or Firm* — Foley & Lardner LLP

(57) ABSTRACT

An adhesion-preventing material having a high adhesion-preventing effect has been demanded. An adhesion-preventing material including a sterilized biocompatible sponge-like laminate, wherein the sponge-like laminate comprises a sponge-like first layer and a sponge-like second layer each of which is at least partially crosslinked with a curing agent and comprises a low-endotoxin alginic acid monovalent metal salt, the alginic acid monovalent metal salt in the first layer has a weight average molecular weight of 10,000 to 2,000,000, the alginic acid monovalent metal salt in the second layer has a weight average molecular weight of 1,000 to 1,000,000, the weight average molecular weights are measured by a GPC-MALS method after a decrosslinking treatment, and the weight average molecular weight of the alginic acid monovalent metal salt in the first layer is higher than that in the second layer.

9 Claims, 13 Drawing Sheets

(56) References Cited

FOREIGN PATENT DOCUMENTS

| WO | WO-2014/093489 A2 | 6/2014 |
| WO | WO-2016/114355 A1 | 7/2016 |
| WO | WO-2017/159700 A1 | 9/2017 |
| WO | WO-2019/138583 A1 | 7/2019 |

OTHER PUBLICATIONS

Lee et al., "Alginate: Properties and biomedical applications", Prag Polym Sci. Jan; 37(1): 106-126. (2012).
Namba et al., "Modulation of Peritendinous Adhesion Formation by Alginate Solution in a Rabbit Flexor Tendon Model," J. Biomed. Mater. Res. Part B: Applied Biomater., 2007, 80(1):273-279.
Non-Final Office Action on U.S. Appl. No. 16/961,080 dated Oct. 16, 2023.

ADHESION-PREVENTING COMPOSITION

CROSS-REFERENCE TO RELATED APPLICATIONS

This application is a Continuation of U.S. application Ser. No. 16/316,097, which is the U.S. National Stage of PCT/JP2017/025614, filed Jul. 13, 2017, which claims priority to JP 2016-138666, filed Jul. 13, 2016.

FIELD OF THE INVENTION

The present invention relates to an adhesion-preventing material, a method for producing the same and a sponge-like laminate.

BACKGROUND ART

Adhesions refer to a state where surfaces of tissues that should be separated from each other are connected or fused to each other via fibrous tissue. Adhesions occur in association with injury or inflammation upon which an exudate containing fibrin is emitted on the surface of the tissue, where this exudate is organized such that the tissue surfaces are connected or fused. Adhesions are caused by an injury generated on a surface of a tissue upon a surgical operation, inflammation caused by an injury, and inflammation caused by drying of a tissue surface upon a surgical operation.

Adhesions sometimes cause infertility, bowel passing disorder and chronic pelvic pain. Moreover, in order to separate adhesions that were caused after a surgical operation, another surgical operation may be required. For example, while multiple times of operations may be effective for a recurrent case of liver cancer, judgement of the propriety of a repeated surgery, risks of the treatment, an amount of bleeding upon the operation, operation time and the like are all largely dependent on the prevention of adhesions following the previous operation. Accordingly, there is a need for preventing adhesions and various means have been adopted to date for preventing adhesions.

Some of such means for preventing adhesions involve providing a physical barrier between an injury or an inflammation site and the adjacent tissue to prevent the tissues from connecting or fusing with each other. A sheet-like barrier is known as such a physical barrier.

Specifically, examples of such a sheet-like barrier include a polytetrafluoroethylene (PTFE) film (Preclude (trade name) (WL Gore and Associates, Inc.)), a sheet containing hyaluronic acid (HA) and carboxymethyl cellulose (CMC) (Seprafilm (trade name) (Genzyme GmbH)), and an oxidized regenerated cellulose sheet (INTERCEED (trade name) (Johnson & Johnson)). Since the PTFE film among them is not biodegradable, it has a problem of remaining in the body. On the other hand, the sheet containing HA and CMC as well as the oxidized regenerated cellulose sheet are biodegradable but they are unable to completely prevent serious adhesions such as an adhesion caused after hepatic resection, and thus they require further improvement to be effective in adhesion prevention.

Now, it is known to make a biocompatible material selected from proteins such as collagen or polysaccharides such as carboxymethyl cellulose, hyaluronic acid or alginic acid into a sheet or particles that can be used as a medical absorbing material, a medical patch, an adhesion-preventing material, a biological tissue reinforcement material or the like (Patent Documents 1-6).

PRIOR ART DOCUMENTS

Patent Documents

Patent Document 1: Japanese Unexamined Patent Application Publication No. Showa 48-79870
Patent Document 2: Japanese Unexamined Patent Application Publication No. 2003-126235
Patent Document 3: International Patent Application Publication No. WO 2005/26214
Patent Document 4: Japanese Unexamined Patent Application Publication No. 2011-25013
Patent Document 5: Japanese Unexamined Patent Application Publication No. 2013-165884
Patent Document 6: Japanese Unexamined Patent Application Publication (Translation of PCT) No. 2016-502874

SUMMARY OF INVENTION

Problem to be Solved by Invention

Under such circumstances, there has been a need for an adhesion-preventing material that has at least one of the following performances: highly effective in preventing adhesions; capable of suppressing both adhesion of a wound and de novo adhesion; has no adverse effect on the living body applied; does not interfere with healing of a wound; can be used for intestinal anastomosis or the like; allows easy application via a trocar upon an endoscopic surgery; capable of being reattached to adjust the attached position; and the like.

Means for Solving Problem

The present inventors have gone through intensive studies on an adhesion-preventing material that has both advantages of a film (sheet)-like adhesion-preventing material and a spray (liquid/gel) adhesion-preventing material in animal adhesion models assuming various clinical operations. As a result, they found that a biocompatible sponge-like adhesion-preventing material comprising a first layer and a second layer with different dissolution rates, specifically, an adhesion-preventing material comprising a biocompatible sponge-like laminate that includes a first sponge-like layer containing a low-endotoxin monovalent metal salt of alginic acid with a relatively high weight average molecular weight and a second sponge-like layer containing a low-endotoxin monovalent metal salt of alginic acid with a relatively low weight average molecular weight, not only prevents adhesion at the surgical site but also effective in preventing adhesions over a wide area of the applied region, thereby accomplishing the present invention.

Thus, the present invention is as follows.

[1-1] An adhesion-preventing material comprising a sterilized biocompatible sponge-like laminate that includes first and second sponge-like layers containing low-endotoxin monovalent metal salts of alginic acid which are at least partially crosslinked with a curing agent, wherein a weight average molecular weight of the monovalent metal salt of alginic acid in the first layer is 10,000-2,000,000, a weight average molecular weight of the monovalent metal salt of alginic acid in the second layer is 1,000-1,000,000, the weight average molecular weights are measured by GPC-MALS method following a decrosslinking treatment, and the weight average molecular weight of the monovalent metal salt of alginic acid in the first layer is higher than the weight average molecular weight of the monovalent metal salt of alginic acid in the second layer.

[1-1a] An adhesion-preventing material comprising a biocompatible sponge-like laminate that includes a first sponge-like layer containing a low-endotoxin monovalent metal salt of alginic acid with a weight average molecular weight of 10,000-2,000,000 and a second sponge-like layer containing a low-endotoxin monovalent metal salt of alginic acid with a weight average molecular weight of 1,000-1,000,000, wherein the weight average molecular weights are measured by GPC-MALS method, and the weight average molecular weight of the monovalent metal salt of alginic acid in the first layer is higher than that in the second layer.

[1-2] The adhesion-preventing material according to either one of [1-1] and [1-1a] above, wherein either one of the first layer and the second layer contains a curing agent.

[1-3] The adhesion-preventing material according to any one of [1-1]-[1-2] above, wherein both of the first layer and the second layer contain a curing agent.

[1-4] The adhesion-preventing material according to any one of [1-1]-[1-3] above, wherein the total amount of the low-endotoxin monovalent metal salts of alginic acid used in the first layer and the second layer is in a range of 0.1 mg/cm$^2$-3 mg/cm$^2$.

[1-5] The adhesion-preventing material according to any one of [1-1]-[1-4] above, wherein the endotoxin content of the monovalent metal salts of alginic acid in the first layer and the second layer is 500 EU/g or less.

[1-6] The adhesion-preventing material according to any one of [1-1]-[1-5] above, wherein the monovalent metal salts of alginic acid in the first layer and the second layer are sodium alginate or potassium alginate.

[1-7] The adhesion-preventing material according to any one of [1-1]-[1-6] above, wherein the curing agent in the first layer and the second layer is at least one metal ionic compound selected from the group consisting of $CaCl_2$, $CaSO_4$, $ZnCl_2$, $SrCl_2$, $FeCl_3$ and $BaCl_2$.

[1-8] The adhesion-preventing material according to any one of [1-1]-[1-7] above, which is for use in being applied such that the first layer faces the surface of a wound.

[1-9] The adhesion-preventing material according to any one of [1-1]-[1-7] above, wherein the sponge-like laminate is sterilized by electron beam and/or gamma irradiation at an absorbed dose of 10 kGy-150 kGy.

[1-10] An adhesion-preventing material comprising a biocompatible sponge-like laminate which includes a first layer and a second layer each containing a low-endotoxin monovalent metal salt of alginic acid which is at least partially crosslinked with a curing agent, wherein a dissolution rate of the first layer is slower than that of the second layer.

[1-10a] An adhesion-preventing material comprising a biocompatible sponge-like laminate which includes a first layer and a second layer each containing a low-endotoxin monovalent metal salt of alginic acid, wherein a dissolution rate of the first layer is slower than that of the second layer.

[1-11] The adhesion-preventing material according to either one of [1-10] and [1-10a] above, wherein, in a dissolution test that uses elution of a monovalent metal salt of alginic acid in a phosphate buffer solution at pH7.5 as an indicator, a ratio of the elution amount of the monovalent metal salt of alginic acid in the first layer is less than 50% after an hour and less than 70% after two hours following the start of the measurement, when taking the elution amount of the monovalent metal salt of alginic acid in the second layer as a base of 100%.

[1-12] The adhesion-preventing material according to either one of [1-10] and [1-10a] above, wherein, in a dissolution test that uses elution of a monovalent metal salt of alginic acid in a phosphate buffer solution at pH7.5 as an indicator, the monovalent metal salt of alginic acid in the first layer is eluted for 25±10 wt % within an hour and for 80±10 wt % within 4 hours while the monovalent metal salt of alginic acid in the second layer is eluted for 70±10 wt % within an hour and for 90±10 wt % within 4 hours.

[1-13] The adhesion-preventing material according to any one of [1-1]-[1-12] above, wherein the sponge-like laminate is pressed.

[2-1] A method for preventing an adhesion, comprising a step of applying a sterilized biocompatible sponge-like laminate that includes first and second sponge-like layers containing low-endotoxin monovalent metal salts of alginic acid which are at least partially crosslinked with a curing agent, wherein a weight average molecular weight of the monovalent metal salt of alginic acid in the first layer is 10,000-2,000,000, a weight average molecular weight of the monovalent metal salt of alginic acid in the second layer is 1,000-1,000,000, the weight average molecular weights are measured by GPC-MALS method following a decrosslinking treatment, and the weight average molecular weight of the monovalent metal salt of alginic acid in the first layer is higher than the weight average molecular weight of the monovalent metal salt of alginic acid in the second layer, to a subject in need of adhesion prevention such that the first layer faces the surface of a wound.

[2-1a] A method for preventing an adhesion, comprising a step of applying a biocompatible sponge-like laminate, including a first sponge-like layer containing a low-endotoxin monovalent metal salt of alginic acid with a weight average molecular weight of 10,000-2,000,000 and a second sponge-like layer containing a low-endotoxin monovalent metal salt of alginic acid with a weight average molecular weight of 1,000-1,000,000, wherein the molecular weights are measured by GPC-MALS method, and the weight average molecular weight of the monovalent metal salt of alginic acid in the first layer is higher than that in the second layer, to a subject in need of adhesion prevention.

[2-2] The method for preventing an adhesion according to either one of [2-1] and [2-1a] above, wherein either one of the first layer and the second layer contains a curing agent.

[2-3] The method for preventing an adhesion according to any one of [2-1]-[2-2] above, wherein both of the first layer and the second layer contain a curing agent.

[2-4] The method for preventing an adhesion according to any one of [2-1]-[2-3] above, wherein the total amount of the low-endotoxin monovalent metal salts of alginic acid used in the first layer and the second layer is in a range of 0.1 mg/cm$^2$-3 mg/cm$^2$.

[2-5] The method for preventing an adhesion according to any one of [2-1]-[2-4] above, wherein the endotoxin content of the monovalent metal salts of alginic acid in the first layer and the second layer is 500 EU/g or less.

[2-6] The method for preventing an adhesion according to any one of [2-1]-[2-5] above, wherein the monovalent metal salts of alginic acid in the first layer and the second layer are sodium alginate or potassium alginate.

[2-7] The method for preventing an adhesion according to any one of [2-1]-[2-6] above, wherein the curing agent in the first layer and the second layer is at least one metal ionic compound selected from the group consisting of $CaCl_2$, $CaSO_4$, $ZnCl_2$, $SrCl_2$, $FeCl_3$ and $BaCl_2$.

[2-8] The method for preventing an adhesion according to any one of [2-1]-[2-7] above, wherein the sponge-like laminate is sterilized by electron beam and/or gamma irradiation at an absorbed dose of 10 kGy-150 kGy.

[2-9] A method for preventing an adhesion, comprising a step of applying a biocompatible sponge-like laminate which includes a first layer and a second layer each containing a low-endotoxin monovalent metal salt of alginic acid which is at least partially crosslinked with a curing agent, wherein a dissolution rate of the first layer is slower than that of the second layer, to a subject in need of adhesion prevention.

[2-9a] A method for preventing an adhesion, comprising a step of applying a biocompatible sponge-like laminate which includes a first layer and a second layer each containing a low-endotoxin monovalent metal salt of alginic acid, wherein a dissolution rate of the first layer is slower than that of the second layer, to a subject in need of adhesion prevention.

[2-10] The method for preventing an adhesion according to either one of [2-9] and [2-9a] above, wherein, in a dissolution test that uses elution of a monovalent metal salt of alginic acid in a phosphate buffer solution at pH7.5 as an indicator, a ratio of the elution amount of the monovalent metal salt of alginic acid in the first layer is less than 50% after an hour and less than 70% after two hours following the start of the measurement, when taking the elution amount of the monovalent metal salt of alginic acid in the second layer as a base of 100%.

[2-11] The method for preventing an adhesion according to either one of [2-9] and [2-9a] above, wherein, in a dissolution test that uses elution of a monovalent metal salt of alginic acid in a phosphate buffer solution at pH7.5 as an indicator, the monovalent metal salt of alginic acid in the first layer is eluted for 25±10 wt % within an hour and for 80±10 wt % within 4 hours while the monovalent metal salt of alginic acid in the second layer is eluted for 70±10 wt % within an hour and for 90±10 wt % within 4 hours.

[2-12] The method for preventing an adhesion according to any one of [2-1]-[2-11] above, wherein the sponge-like laminate is pressed.

[3-1] A method for producing an adhesion-preventing material comprising a biocompatible sponge-like laminate, the method comprising the steps of:

(1) curing a low-endotoxin monovalent metal salt of alginic acid with a weight average molecular weight of 10,000-2,000,000 with a curing agent;

(2) freezing the cured monovalent metal salt of alginic acid;

(3) curing a low-endotoxin monovalent metal salt of alginic acid with a weight average molecular weight of 1,000-1,000,000 with a curing agent on the monovalent metal salt of alginic acid obtained in (2) to obtain a laminate; and (4) lyophilizing the resulting laminate to obtain a sponge-like laminate, wherein the molecular weights are measured by GPC-MALS method, the sponge-like laminate includes a first sponge-like layer containing the low-endotoxin monovalent metal salt of alginic acid with a weight average molecular weight of 10,000-2,000,000 and a second sponge-like layer containing the low-endotoxin monovalent metal salt of alginic acid with a weight average molecular weight of 1,000-1,000,000, and the weight average molecular weight of the monovalent metal salt of alginic acid in the first layer is higher than that in the second layer.

[3-2] The method for producing the adhesion-preventing material according to [3-1] above, wherein the sponge-like laminate is sterilized by electron beam and/or gamma irradiation at an absorbed dose of 10 kGy-150 kGy.

[3-3] The method for producing the adhesion-preventing material according to either one of [3-1] and [3-2] above, further comprising a step of pressing the laminate obtained in (4).

[4-1] A biocompatible sponge-like laminate obtained by the following steps (1)-(4):

(1) curing a low-endotoxin monovalent metal salt of alginic acid with a weight average molecular weight of 10,000-2,000,000 with a curing agent;

(2) freezing the cured monovalent metal salt of alginic acid;

(3) curing a low-endotoxin monovalent metal salt of alginic acid with a weight average molecular weight of 1,000-1,000,000 with a curing agent on the monovalent metal salt of alginic acid obtained in (2) to obtain a laminate; and (4) lyophilizing the resulting laminate to obtain a sponge-like laminate, wherein the molecular weights are measured by GPC-MALS method, the sponge-like laminate includes a first sponge-like layer containing the low-endotoxin monovalent metal salt of alginic acid with a weight average molecular weight of 10,000-2,000,000 and a second sponge-like layer containing the low-endotoxin monovalent metal salt of alginic acid with a weight average molecular weight of 1,000-1,000,000, and the weight average molecular weight of the monovalent metal salt of alginic acid in the first layer is higher than that in the second layer.

[4-2] The sponge-like laminate according to [4-1] above, which is used as an adhesion-preventing material.

[4-3] The sponge-like laminate according to either one of [4-1] and [4-2] above, wherein the sponge-like laminate is sterilized by electron beam and/or gamma irradiation at an absorbed dose of 10 kGy-150 kGy.

[4-4] The sponge-like laminate according to any one of [4-1]-[4-3] above, further comprising a step of pressing the laminate obtained in (4).

[5-1] A combination of feedstocks for producing an adhesion-preventing material, the combination comprising a first feedstock containing a low-endotoxin monovalent metal salt of alginic acid with a weight average molecular weight of 10,000-2,000,000 and a second feedstock containing a low-endotoxin monovalent metal salt of alginic acid with a weight average molecular weight of 1,000-1,000,000, wherein the weight average molecular weight of the first feedstock is higher than that of the second feedstock.

[5-2] The combination of feedstocks according to [5-1] above, which is used for producing a sponge-like laminate.

Effect of the Invention

The present invention can provide an adhesion-preventing material that has at least one of the following performances: highly effective in preventing adhesions; capable of suppressing both adhesion of a wound and de novo adhesion; has no adverse effect on a living body applied; does not interfere with healing of a wound; can be used for intestinal anastomosis or the like; allows easy application via a trocar upon an endoscopic surgery; capable of being reattached to adjust the attached position; and the like.

BRIEF DESCRIPTION OF THE DRAWINGS

(FIG. 3A) Number of individuals that formed adhesion on the resected surfaces, (FIG. 3B) grade of the resected surfaces, and (FIG. 3C) extent of the resected surfaces (mm). $**p<0.01$, $*p<0.05$.

(FIG. 4A) Number of individuals that formed adhesion on the unresected surfaces, (FIG. 4B) grade of the unresected surfaces, and (FIG. 4C) extent of the unresected surfaces (mm). $**p<0.01$, $*p<0.05$.

(FIG. 5A) Change in body weight, and (FIG. 5B) spleen weight.

(FIG. 6A) Number of individuals that formed adhesion on the resected surfaces, (FIG. 6B) grade of the resected surfaces, and (FIG. 6C) extent of the resected surfaces (mm). $**p<0.01$, $*p<0.05$.

(FIG. 7A) Number of individuals that formed adhesion on the unresected surfaces, (FIG. 7B) grade of the unresected surfaces, and (FIG. 7C) extent of the unresected surfaces (mm). $**p<0.01$, $*p<0.05$.

(FIG. 8A) Change in body weight, and (FIG. 8B) spleen weight.

MODE FOR CARRYING OUT THE INVENTION

Figure 1:
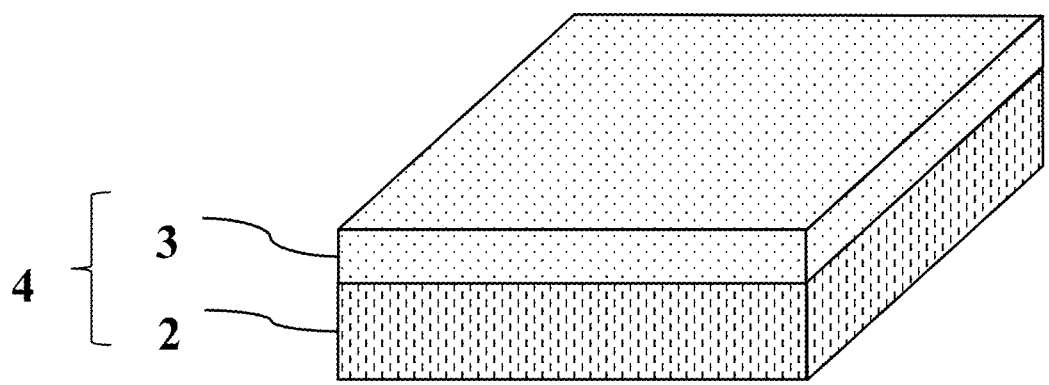
FIG. 1 A view showing an example of an adhesion-preventing material.

Hereinafter, the present invention will be described in detail. The following embodiments are illustrations of the present invention, and the present invention may be carried out in various embodiments without departing from the gist thereof.

1. Adhesion Prevention

"Adhesions" refer to a state where surfaces of tissues that should be separated from each other are connected or fused to each other via fibrous tissue. Adhesions are caused by an injury generated on a surface of a tissue upon a surgical operation, inflammation caused by an injury, and inflammation caused by drying of a tissue surface upon a surgical operation. Adhesions are formed in association with such injury or inflammation upon which an exudate containing fibrin is emitted on a surface of a tissue, where this exudate is organized such that the tissue surfaces are connected or fused.

"Adhesion prevention" means to reduce formation of adhesions. Adhesion prevention does not necessarily require complete prevention of formation of adhesions, and may apply as long as formation of adhesion is prevented compared to a state where an adhesion-preventing material of the present invention is not applied. Specifically, "adhesion prevention" may also refer to as amelioration of adhesions, which may mean, for example, amelioration of at least one selected from frequency, area and degree of the adhesions. "Adhesion prevention" may be, for example, lowering of an average adhesion grade as compared to an average adhesion grade without application of the adhesion-preventing material of the present invention when adhesion grade is evaluated as described in the example. Alternatively, "adhesion prevention" may be, for example, lowering of the average adhesion extent as compared to an average adhesion extent without application of the adhesion-preventing material of the present invention when adhesion extent is evaluated as described in the example. "Adhesion prevention" preferably refers to prevention of adhesion resulting from a surgical operation, and more preferably refers to prevention of peritoneal adhesion resulting from a surgical operation. Specifically, "adhesion prevention" preferably refers to adhesion prevention following a surgery.

In addition, as described in the examples, targeted adhesions may be an adhesion of a site of a target organ resected upon a surgery and de novo adhesions (adhesions formed with various sites in the periphery, the abdominal cavity and the body other than the surgical site).

2. Adhesion-Preventing Material

The present invention provides an adhesion-preventing material comprising a biocompatible sponge-like laminate that includes first and second sponge-like layers containing low-endotoxin monovalent metal salts of alginic acid which are at least partially crosslinked with a curing agent, wherein the first sponge-like layer contains a low-endotoxin monovalent metal salt of alginic acid with a relatively high weight average molecular weight and the second sponge-like layer contains a low-endotoxin monovalent metal salt of alginic acid with a relatively low weight average molecular weight (hereinafter, sometimes referred to as "an adhesion-preventing material A"). The weight average molecular weights of the low-endotoxin monovalent metal salts of alginic acid used in the first layer and the second layer are, for example, 10,000-2,000,000 and 1,000-1,000,000, respectively. Such weight average molecular weights are measured by GPC-MALS method following a decrosslinking treatment, for example, following dissolution in a solution of a chelating agent.

Herein, a sign "–" used for a numerical range refers to "the lower limit value to the upper limit value" where the numerical values on both sides of the sign are inclusive in said range.

The adhesion-preventing material A contains low-endotoxin monovalent metal salts of alginic acid with different molecular weights in the first layer and the second layer of the sponge-like laminate. Specifically, the weight average molecular weight of the monovalent metal salt of alginic acid in the first layer is higher than that in the second layer. A dissolution rate of a layer containing a monovalent metal salt of alginic acid becomes slower for a larger weight average molecular weight of the monovalent metal salt of alginic acid whereas the dissolution rate becomes faster for a smaller weight average molecular weight. Accordingly, the adhesion-preventing material A of the present invention is applied such that the first layer faces the wound while the second layer faces the abdominal cavity, expecting that the first layer remains at the wound while the second layer dissolves relatively faster to suppress the general adhesions in the abdominal cavity.

Furthermore, the present invention provides an adhesion-preventing material comprising a biocompatible sponge-like laminate which includes a first layer and a second layer each containing a low-endotoxin monovalent metal salt of alginic acid which is at least partially crosslinked with a curing agent, wherein dissolution rates of the first layer and the second layer are different ("adhesion-preventing material B"). Specifically, the dissolution rate of the first layer is slower than that of the second layer. The dissolution rate of the first layer may be made slower than the dissolution rate of the second layer, for example, by making the weight average molecular weight of the monovalent metal salt of alginic acid in the first layer to be higher than that in the second layer like the adhesion-preventing material A, or by making the crosslinking degree of the monovalent metal salt of alginic acid in the first layer to be higher than that in the second layer by changing the type of the crosslinking agent, by changing the concentration of the crosslinking agent, or the like.

For the adhesion-preventing material B, the ratio of the elution amount of the monovalent metal salt of alginic acid in the first layer is preferably less than 50% after an hour and less than 70% after two hours following the start of the measurement in a dissolution test that uses elution of the monovalent metal salt of alginic acid as an indicator, when taking the elution amount of the monovalent metal salt of alginic acid in the second layer as a base of 100%.

In another preferable example, in the adhesion-preventing material B, the monovalent metal salt of alginic acid in the first layer is eluted for 25±10 wt % within an hour and for 80±10 wt % within 4 hours while the monovalent metal salt of alginic acid in the second layer is eluted for 70±10 wt % within an hour and for 90±10 wt % within 4 hours, in a dissolution test that uses elution of the monovalent metal salt of alginic acid as an indicator. The details of the dissolution test will be described in the examples below.

Herein, the "adhesion-preventing material A" and the "adhesion-preventing material B" may sometimes collectively be referred to as an "adhesion-preventing material". The "first layer" refers to a layer that becomes a lower layer when the sponge-like laminate is applied to a subject, namely, a layer that makes contact with a surface of a tissue for application in the subject. The "second layer" refers to a layer that becomes an upper layer when the sponge-like laminate is applied to a subject, namely, a layer that does not make contact with a surface of a tissue for application in the subject. The phrase "biocompatible" means that it can be placed on a surface of a tissue to be applied as a medical material.

A biocompatible sponge-like laminate used as an adhesion-preventing material may have, in addition to the above-described first and second layers, a third layer containing any component, or may have a multilayer structure. In addition, the sponge-like laminate may also comprise a structure in which there is no clear boundary between the layers where the molecular weight continuously gradually increases or decreases.

An exemplary adhesion-preventing material is shown in FIG. 1. An adhesion-preventing material 1 comprises a sponge-like laminate 4 including a first layer 2 and a second layer 3. Each of the first layer 2 and the second layer 3 is a sponge-like layer. The term "sponge-like" refers to a porous state.

The shape of the biocompatible sponge-like laminate is not particularly limited and may suitably be selected considering the area, shape, unevenness and the like of the surface to be applied. The shape of the sponge-like laminate may be, for example, a plate as shown in FIG. 1, or it may have a shape such as a disc, a cylinder, a rectangular cuboid or the like. Preferably, it is a plate or a disc. If it is a plate or a disc, the size of the plate or the disc is not particularly limited since the adhesion-preventing material can further be cut in accordance with the area, shape, unevenness or the like of the surface applied before being applied to the surface. For example, where a shape of a plate is expressed by length×width×height (thickness), the length and the width are not particularly limited while the height (thickness) is preferably 0.2 mm-30 mm, more preferably 0.3 mm-15 mm, and still more preferably 0.5 mm-10 mm. Yet still more preferably, in addition to such a height (thickness), the length and the width are 1 mm-300 mm×1 mm-300 mm, particularly preferably 3 mm-200 mm×3 mm-200 mm, and more preferably 5 mm-150 mm×5 mm-150 mm, respectively. The thickness may not be uniform in which case the laminate may have an inclination structure with one thicker end and the other thinner end.

A sponge-like laminate of the adhesion-preventing material of the present invention is highly flexible and hard to break as compared to Seprafilm (trade name).

In some aspects, the sponge-like laminate is pressed. "Pressing" will be described hereinbelow. In a case of a pressed sponge-like laminate, the height (thickness) is preferably 0.02 mm-3 mm, more preferably 0.03 mm-1.5 mm, and still more preferably 0.05 mm-1 mm. More preferably, in addition to such a height (thickness), the length and the width are 1 mm-300 mm×1 mm-300 mm, particularly preferably 3 mm-200 mm×3 mm-200 mm, and more preferably 5 mm-150 mm×5 mm-150 mm, respectively. In some aspects, the thickness after pressing is uniform.

3. Monovalent Metal Salt of Alginic Acid

A "monovalent metal salt of alginic acid" is a water-soluble salt that is formed through ion exchange between a hydrogen atom of carboxylic acid at position 6 of alginic acid and a monovalent metal ion such as $Na^+$ or $K^+$. Specific examples of monovalent metal salts of alginic acid include sodium alginate and potassium alginate, while sodium alginate that can be obtained as a commercially available product is particularly preferable. A solution of a monovalent metal salt of alginic acid forms a gel when mixed with a curing agent.

"Alginic acid" used in the present invention is a biodegradable polymeric polysaccharide, which is a polymer resulting from linear polymerization of two types of uronic acids called D-mannuronic acid (M) and L-guluronic acid (G). More specifically, alginic acid is a block copolymer which has a homopolymer fraction of D-mannuronic acid (MM fraction), a homopolymer fraction of L-guluronic acid (GG fraction) and a fraction having randomly arranged D-mannuronic acids and L-guluronic acids (MG fraction), arbitrarily linked together. A composite ratio of D-mannuronic acid to L-guluronic acid (M/G ratio) of alginic acid varies primarily according to the type of a biological origin such as seaweed, and is affected by the habitat and seasons of said biological origin. The M/G ratio widely ranges from about 0.4 that is rich in G to about 5 that is rich in M.

Since a monovalent metal salt of alginic acid is a polymeric polysaccharide, it is difficult to accurately determine the molecular weight thereof. Thus, a molecular weight of a polymeric substance derived from a natural origin is known to vary depending on the measurement method.

An absolute weight average molecular weight can be measured by GPC-MALS method. A weight average molecular weight of a monovalent metal salt of alginic acid that can be used as a feedstock of the first layer of the sponge-like laminate is, for example, 10,000-2,000,000, preferably 15,000-1,500,000, more preferably 20,000-1,000,000, and particularly preferably 25,000-500,000 as measured by GPC-MALS method. In addition to said first layer, a weight average molecular weight of the second layer is, for example, 1,000-1,000,000, preferably 1,000-500,000, more preferably 2,000-250,000, and particularly preferably 3,000-100,000 as measured by GPC-MALS method.

In some aspects, for example, after sterilization by electron beam and/or gamma-ray irradiation, a weight average molecular weight of the first layer of the sponge-like laminate is, for example, 10,000-300,000, preferably 10,000-200,000, more preferably 10,000-100,000, and particularly preferably 10,000-80,000 as measured by GPC-MALS method. In addition to said first layer, a weight average molecular weight of the second layer is, for example, 1,000-100,000, preferably 1,000-80,000, more preferably 2,000-60,000, and particularly preferably 3,000-60,000 as measured by GPC-MALS method.

For a monovalent metal salt of alginic acid which is at least partially crosslinked with a curing agent, the weight average molecular weight can be determined as a monovalent metal salt of alginic acid that is not crosslinked by GPC-MALS method following any decrosslinking treatment. For example, the decrosslinking treatment may be dissolution in any chelating agent, for example, a solution of a chelating agent such as EDTA (ethylenediaminetetraacetic acid) or phytic acid. Preferably, EDTA is used as the chelating agent.

The weight average molecular weight of the monovalent metal salt of alginic acid in the first layer of the sponge-like laminate is higher than that in the second layer. The weight average molecular weight of the monovalent metal salt of alginic acid in the feedstock of the sponge-like laminate or in the first layer of the sponge-like laminate is higher than that in the second layer, for example, by 1,000-1,000,000, preferably by 2,000-500,000, and more preferably by 3,000-300,000.

In general, a measurement error of 10-20 wt % may be expected when a molecular weight of a polymeric polysaccharide is calculated by a technique as described above. Thus, the value of 10,000 may vary in a range of about 8,000-12,000, the value of 100,000 may vary in a range of about 80,000-120,000, the value of 200,000 may vary in a range of about 160,000-240,000, the value of 400,000 may vary in a range of about 320,000-480,000, and the value of 500,000 may vary in a range of about 400,000-600,000.

A molecular weight of alginic acid may be measured according to a common method. Typical conditions upon employing GPC-MALS for molecular weight measurement are as described herein in Example 1. As the detector, for example, a RI detector and a light scattering detector (MALS) may be used.

Although an alginic acid that is extracted from a brown alga initially has a large molecular weight, the molecular weight gradually becomes smaller during the processes of heat drying, purification and the like. Alginic acids having different molecular weights can be produced by techniques like management of conditions such as the temperature or the like during the production steps, selection of the brown alga as the raw material, fractionation based on molecular weights during the production process and the like. Furthermore, an alginic acid having a molecular weight of interest can be obtained by mixing with an alginic acid from other lot having a different molecular weight.

A monovalent metal salt of alginic acid used in the present invention is subjected to a low endotoxin treatment. The low endotoxin treatment can be performed according to a known method or a method pursuant thereto. For example, the treatment can be carried out according to the method of Suga et al. involving purification of sodium hyaluronate (see, for example, Japanese Unexamined Patent Application Publication No. Heisei 9-324001), the method of Yoshida et al., involving purification of β1,3-glucan (see, for example, Japanese Unexamined Patent Application Publication No. Heisei 8-269102), the method of William et al. involving purification of a biopolymer salt such as alginate or gellan gum (see, for example, Japanese Unexamined Patent Application Publication (Translation of PCT Publication) No. 2002-530440), the method of James et al. involving purification of a polysaccharide (see, for example, pamphlet of International Publication No. 93/13136), the method of Lewis et al. (see, for example, specification of U.S. Pat. No. 5,589,591), the method of Hermanfranck et al. involving purification of alginate (see, for example, Appl Microbiol Biotechnol (1994) 40:638-643) or methods pursuant thereto. The low endotoxin treatment of the present invention is not limited thereto, and can be carried out by a known method such as washing, filtration with a filter (such as an endotoxin-removing filter or an electrically-charged filter), ultrafiltration, purification with a column (such as an endotoxin adsorption affinity column, a gel filtration column or an ion-exchange resin column), adsorption to a hydrophobic substance, a resin or activated charcoal, a treatment with an organic solvent (extraction with an organic solvent, deposition/precipitation through addition of an organic solvent, or the like), a surfactant treatment (see, for example, Japanese Unexamined Patent Application Publication No. 2005-036036), or an appropriate combination thereof. The steps in these treatments may appropriately be combined with a known method such as centrifugation. Preferably, the treatment is suitably selected according to the type of the alginic acid.

An endotoxin level can be confirmed according to a known method. For example, it can be measured by a method using a limulus agent (LAL), or a method using Endospecy (registered trademark) ES-24S set (Seikagaku Corporation).

Although a method for treating endotoxin of a monovalent metal salt of alginic acid used in the present invention is not particularly limited, the resulting endotoxin content of a bioabsorbable polysaccharide is preferably 500 endotoxin unit (EU)/g or less, more preferably 100 EU/g or less, still more preferably 50 EU/g or less, and particularly preferably 30 EU/g or less upon an endotoxin measurement using a limulus agent (LAL). Sodium alginate that has been subjected to a low endotoxin treatment is available, for example, as a commercially available product such as Sea Matrix (registered trademark) (Mochida Pharmaceutical Co., Ltd.) and PRONOVA™ UP LVG (FMC BioPolymer).

The amount of the monovalent metal salt of alginic acid used in the sponge-like laminate may appropriately be selected considering the adhesion prevention effect. The total amount of the monovalent metal salts of alginic acid used in the first layer and the second layer of the sponge-like laminate may be, for example, 0.1 mg/cm$^2$-10.0 mg/cm$^2$, preferably 0.1 mg/cm$^2$-3.0 mg/cm$^2$, more preferably 0.5 mg/cm$^2$-2.5 mg/cm$^2$, still more preferably 1.8 mg/cm$^2$-2.2 mg/cm$^2$, and particularly preferably 2.0 mg/cm$^2$. If the total amount of the monovalent metal salts of alginic acid used in the first layer and the second layer of the sponge-like laminate is 1.0 mg/cm$^2$-3.0 mg/cm$^2$, a higher adhesion prevention effect can be expected. The risk of adverse events such as accumulation in the living body or enlargement of a specific organ is less if the amount used is 10.0 mg/cm² or less while a satisfactory adhesion prevention effect can be expected if the amount used is 0.1 mg/cm² or more.

The ratio of the amounts of the monovalent metal salts of alginic acid used in the first layer and the second layer (weight ratio) is preferably 1:20-20:1, more preferably 1:5-5:1, still more preferably 1:3-3:1, and particularly preferably 1:2-2:1.

4. Curing Agent (Crosslinking Agent)

The adhesion-preventing material may contain a curing agent in either one of the first layer and the second layer (in other words, either one of the first layer and the second layer may not contain a curing agent), or both of the first layer and the second layer may contain a curing agent.

Alternatively, neither of the first layer nor the second layer of the adhesion-preventing material may contain a curing agent.

In some aspects, the first layer and the second layer are at least partially crosslinked with a curing agent.

The curing agent allows hardening by crosslinking a solution of the monovalent metal salt of alginic acid. Examples of the curing agent include bivalent or higher metal ion compounds of $Ca^{2+}$, $Mg^{2+}$, $Ba^{2+}$, $Sr^{2+}$, $Zn^{2+}$ and $Fe^{3+}$ and crosslinking reagents that have two to four amino groups within their molecules. More specifically, examples of bivalent or higher metal ion compounds include $CaCl_2$, $MgCl_2$, $CaSO_4$, $ZnCl_2$, $FeCl_3$, $BaCl_2$ and $SrCl_2$ (preferably, $CaCl_2$, $CaSO_4$, $ZnCl_2$, $SrCl_2$, $FeCl_3$, $BaCl_2$, etc.), while examples of crosslinking reagents having two to four amino groups within their molecules include diaminoalkanes optionally having a lysyl group ($-COCH(NH_2)-(CH_2)_4-NH_2$) on a nitrogen atom, that is, diaminoalkane and derivatives thereof that form lysyl amino groups by substituting an amino group with a lysyl group, specific examples being diaminoethane, diaminopropane and N-(lysyl)-diaminoethane.

The amount of the curing agent used in the first layer and the second layer is preferably adjusted suitably in accordance with the amount or the molecular weight of the monovalent metal salt of alginic acid. In a case where a curing agent is used, the amount of the curing agent used in the first layer is, for example, 0.1 μmol/cm²-100 μmol/cm², and preferably 0.5 μmol/cm²-2.0 μmol/cm². In a case where a curing agent is used, the amount of the curing agent used in the second layer is, for example, 0.1 μmol/cm²-10 μmol/cm², and preferably 0.6 μmol/cm²-2.4 μmol/cm².

5. Method for Producing Adhesion-Preventing Material

An adhesion-preventing material comprising a biocompatible sponge-like laminate or a biocompatible sponge-like laminate may, for example, be produced through the following steps:

(1) curing a low-endotoxin monovalent metal salt of alginic acid with a weight average molecular weight of 10,000-2,000,000 with a curing agent;

(2) freezing the cured monovalent metal salt of alginic acid;

(3) curing a low-endotoxin monovalent metal salt of alginic acid with a weight average molecular weight of 1,000-1,000,000 with a curing agent on the monovalent metal salt of alginic acid obtained in (2) to obtain a laminate; and (4) lyophilizing the resulting laminate to obtain a sponge-like laminate, In step (1) above, first, a solution of a low-endotoxin monovalent metal salt of alginic acid with a weight average molecular weight of 10,000-2,000,000 (hereinafter, referred to as a "first alginic acid salt") and a solution of a curing agent are prepared. The solution of the first alginic acid salt and the solution of the curing agent can be prepared according to a known method or a method pursuant thereto. While the solvent can be any solvent as long as it is biocompatible, it is preferably an aqueous solvent, for example, purified water, pure water (e.g., distilled water, ion-exchanged water), Milli-Q water, physiological saline, phosphate buffered saline and DMSO, and more preferably pure water. The solvent is preferably one that has been sterilized and that has been subjected to a low endotoxin treatment.

Then, the solution of the first alginic acid salt and the solution of the curing agent can be mixed to cure the first alginic acid salt.

In step (2) above, the first alginic acid salt cured in step (1) is frozen by a common method. Freezing prior to step (3) can decrease the mixed proportion of the first layer and the second layer. The temperature and time of freezing may be, for example, −20° C. for four hours.

In step (3) above, first, a solution of a low-endotoxin monovalent metal salt of alginic acid with a weight average molecular weight of 1,000-1,000,000 (hereinafter, referred to as a "second alginic acid salt") and a solution of a curing agent are prepared. The solution of the second alginic acid salt and the solution of the curing agent can be prepared according to a known method or a method pursuant thereto. The solvent is similar to that described for step (1) above.

Then, the solution of the second alginic acid salt and the solution of the curing agent can be mixed to cure the second alginic acid salt.

The cured second alginic acid salt may further be frozen prior to step (4). The temperature and time of freezing may be, for example, −20° C. for four hours.

In step (4) above, the laminate obtained in step (3) is lyophilized to obtain a sponge-like laminate. Lyophilizing can be carried out by a known method. Conditions for lyophilizing can suitably be adjusted, and lyophilizing may include a primary drying step, a secondary drying step and the like.

Through these steps, a biocompatible sponge-like laminate including a first sponge-like layer containing a first alginic acid salt and a curing agent and a second sponge-like layer containing a second alginic acid salt and a curing agent, wherein the weight average molecular weight of the monovalent metal salt of alginic acid in the first layer is higher than that in the second layer, as well as an adhesion-preventing material comprising said sponge-like laminate can be obtained.

According to the above-described method, the first sponge-like layer containing the first alginic acid salt and the curing agent is prepared at first, and then the second sponge-like layer containing the second alginic acid salt and the curing agent is prepared thereon. Alternatively, the second layer may be prepared at first and then the first layer may be prepared thereon. In this case, the sponge-like laminate may, for example, be produced through the following steps:

(1') curing a second alginic acid salt with a curing agent;

(2') freezing the cured second alginic acid salt;

(3') curing a first alginic acid salt with a curing agent on the second alginic acid salt obtained in (2) to obtain a laminate; and (4') lyophilizing the resulting laminate to obtain a sponge-like laminate, Detailed description of the steps is the same as the above-described steps.

Alternatively, the first alginic acid salt may be cured and lyophilized to prepare a first sponge-like layer while the second alginic acid salt is cured and lyophilized to separately prepare a second sponge-like layer so that the resulting sponge-like layers can be adhered to each other to obtain a sponge-like laminate.

Detailed description of the step is the same as the above-described steps.

An adhesion-preventing material comprising a sponge-like laminate having a desired size, height and shape can be obtained by using a vessel, a mold, a substrate, a porous membrane, a non-woven fabric, a woven fabric or the like having a desired size, height and shape upon curing the first alginic acid salt and the second alginic acid salt.

Preferably, the sponge-like laminate of the adhesion-preventing material is further subjected to a sterilization treatment. Examples of sterilization include, but not limited to, gamma-ray sterilization, electron beam sterilization, ethylene oxide gas sterilization and ethanol sterilization. More preferably, the adhesion-preventing material is subjected to a sterilization treatment by electron beam and/or gamma irradiation. A polymeric material is subjected to an irradiation treatment with a gamma-ray, an electron beam or the like so as to preferably obtain a highly biocompatible medical material with controlled retention in the body (see, for example, Japanese Unexamined Patent Application Publication No. 2000-237294).

Examples of the irradiation conditions upon electron beam and/or gamma-ray sterilization include an absorbed dose of 10 kGy-150 kGy, more preferably 20 kGy-100 kGy, and still more preferably 40 kGy-80 kGy. In another preferable aspect, examples of the irradiation conditions upon electron beam and/or gamma-ray sterilization include an absorbed dose of 20 kGy-80 kGy, 20 kGy-60 kGy or 40 kGy-60 kGy. Electron beam sterilization is more favorable than gamma-ray sterilization.

Some aspects further comprise a step of pressing the laminate obtained, for example, in step (4) above. Pressing can be carried out by holding and applying pressure on the laminate manually or with a press machine. Generally employed steps such as compression and thinning are also included as pressing of the present invention. Examples of the pressure adopted for pressing include 1 kPa-100 MPa, more preferably 10 kPa-80 MPa, and still more preferably 100 kPa-60 Mpa. Manual pressing is carried out with a means that can apply uniform pressure onto the laminate by pressing it with a hand, for example, an acrylic ruler, an acrylic plate, a glass plate, a metal plate or the like. Moreover, an example of the press machine used includes a hot press machine (AH-1T from As One).

6. Usage

The adhesion-preventing material is used by applying it to a subject in need of adhesion prevention. Preferably, the adhesion-preventing material remains on the applied site usually for about a week that is necessary for exhibiting the adhesion prevention effect, then absorbed and decomposed and eventually metabolized/excreted in about 1-2 months, and thus it is highly safety.

The adhesion-preventing material may also be applied to a surface of a wound, for example, a surface of a tissue involved in a surgical operation.

A "tissue involved in a surgical operation" refers to a tissue that has a wound on its surface due to the surgical operation, or a tissue that has inflammation or that has a risk of inflammation due to drying of the surface upon a surgical operation. A tissue involved in a surgical operation is preferably an organ wrapped in peritoneum (for example, stomach, jejunum, ileum, appendix, colon, liver, spleen, duodenum and pancreas). An adhesion-preventing material of a preferable aspect of the present invention is capable of effectively preventing a serious adhesion such as an adhesion occurring after hepatic resection.

To "apply" means to place an adhesion-preventing material on a surface of a wound (for example, a surface of a tissue involved in a surgical operation). Specifically, the adhesion-preventing material is placed on a surface of a wound (for example, a surface of a tissue involved in a surgical operation) such that the surface of the first layer of the sponge-like laminate makes contact with the surface of the wound (for example, the surface of the tissue) while the surface of the second layer faces the opposite side (for example, the abdominal side) of the surface of the wound (for example, the surface of the tissue). Since the first layer of the sponge-like laminate has a relatively high weight average molecular weight, it remains on the surface of the tissue without being decomposed for a sufficient amount of time to prevent adhesion, thereby serving as a physical barrier for the wound surface. Meanwhile, since the second layer of the sponge-like laminate has a relatively low weight average molecular weight, it melts and spreads quickly to exert adhesion prevention for the uninjured surface.

Preferably, the sponge-like laminate of the adhesion-preventing material is highly flexible and hard to break as compared to Seprafilm (trade name). Therefore, in a preferable aspect, application of the adhesion-preventing material is not limited to the surface of the tissue to be applied and, for example, it can also be wound around an intestinal tract upon intestinal anastomosis. In another preferable aspect, it can easily be inserted through a pathway for putting a surgical instrument in and out upon a surgical operation using an endoscope in a subject. In yet another preferable aspect, the adhesion-preventing material can be reattached.

Preferably, the sponge laminate of the adhesion-preventing material can be applied to a wider range of targets for adhesion prevention compared to INTERCEED (trade name).

Preferably, the adhesion-preventing material is prepared in a size appropriate for the area, shape, unevenness and the like of a surface to be applied, and applied onto the surface of the tissue involved in a surgical operation for adhesion prevention. A "subject" may be human or an organism other than human, for example, a bird or a non-human mammal (for example, bovine, monkey, cat, mouse, rat, guinea pig, hamster, pig, dog, rabbit, sheep or horse).

Since the sponge laminate of the adhesion-preventing material can be made compact particularly if the sponge laminate is pressed, the adhesion-preventing material can be applied to the affected area relatively easily, for example, via a trocar or the like upon an endoscopic surgery. Thereafter, the adhesion-preventing material applied to the affected area preferably absorbs moisture present in the affected area or moisture applied to the affected area to restore the thickness.

Similar to Seprafilm (trade name) and INTERCEED (trade name), the adhesion-preventing material can preferably be used safely in a subject.

After application to the surface of the tissue involved in a surgical operation, there is usually no need of suture between the adhesion-preventing material and the surface of the tissue involved in the surgical operation, but if necessary, the adhesion-preventing material may be sutured with the tissue involved in the surgical operation.

Furthermore, a method for preventing an adhesion comprising a step of applying a sponge-like laminate to a subject in need of adhesion prevention is provided. Detail of the method is as described hereinbefore.

Moreover, use of a sponge-like laminate for producing an adhesion-preventing material is provided. Detail of the use is as described hereinbefore.

In addition, a sponge-like laminate for preventing adhesion is provided. Detail of the sponge-like laminate is as described hereinbefore.

7. Co-Administered Drug

Moreover, a co-administered drug, for example, an antibiotic such as streptomycin, penicillin, tobramycin, amikacin, gentamicin, neomycin or amphotericin B or an anti-inflammation drug such as aspirin, a non-steroidal analgesic antipyretic drug (NSAIDs) or acetaminophen may be administered before, simultaneously or after applying the adhesion-preventing material of the present invention to a tissue involved in a surgical operation. These drugs may also be used by being mixed with the adhesion-preventing material of the present invention.

Since the sponge-like laminate is porous and has a water absorbing property, it is easier to carry a drug that can be prepared upon use, for example, as compared to non-porous Seprafilm (trade name). The sponge may be impregnated with a drug solution for administration so that adhesion prevention and topical sustained release of the drug can be realized at the same time upon administration in abdominal cavity, thoracic cavity, cardiac cavity or the like. Moreover, a drug can be carried in layers with different dissolution rates so as to allow sustained release of the drug at a faster sustained release rate and a slower sustained release rate.

All publications cited herein, such as prior art documents, unexamined patent applications, patent publications and other patent documents, are incorporated in their entirety herein by reference.

The present invention will be further described in detail by way of examples, although the present invention should not be limited to these examples.

EXAMPLES

Example 1

Production of Alginic Acid-Layered Sponge

An alginic acid-layered sponge was produced as follows.
[Reagents]
The reagents used for preparing the alginic acid-layered sponge were as follows.
Low-endotoxin sodium alginate was obtained from Mochida Pharmaceutical Co., Ltd.
AL10: (Lot NO. 5K12202), endotoxin level 4 EU/g.
AL500: (Lot NO. BL150713-500), endotoxin level 19 EU/g.
Calcium chloride was obtained from Wako Pure Chemical Industries, Ltd. (Product code: 036-00485).
[Instruments Used]
35 mm untreated dish (IWAKI Product code 1000-035)
Micropipette (Gilson Pipetman (trade name))
Pure water manufacturing equipment (Merck Millipore Elix Essential UV5 (trade name))
Freezer (SHARP SJ-56S (trade name))
Lyophilizer (TAITEC VD-550R (trade name))
[Preparation Procedure]
(1) Preparation of Solution
AL500 was dissolved in pure water at a concentration of 1.0 wt % to prepare an AL500 solution. Similarly, AL10 was dissolved in pure water at a concentration of 1.0 wt % to prepare an AL10 solution. Moreover, calcium chloride was dissolved in pure water to prepare 10 mM and 15 mM aqueous calcium chloride solutions, respectively.

(2) Preparation of AL500 Layer (Lower Layer)

1.0 mL of the AL500 solution and 1.0 mL of the 10 mM aqueous calcium chloride solution were placed into an untreated 35 mm dish using Micropipette and the resultant was homogeneously mixed by pipetting. The resultant was left to stand overnight to allow gelation. The dish was transferred to the freezer to freeze the resultant at −20° C. for four hours.

(3) Lamination of AL10 Layer (Upper Layer)

The dish is taken out from the freezer so as to add 1.0 mL of the AL10 solution and 1.0 mL of the 15 mM aqueous calcium chloride solution onto the frozen AL500 layer using Micropipette and the resultant was homogeneously mixed by pipetting. The dish was again placed in the freezer to freeze the resultant at −20° C. for four hours.

(4) Preparation of Sponge

The frozen dish was placed in the lyophilizer and subjected to lyophilizing for two nights, thereby obtaining an alginic acid-layered sponge of interest.

The alginic acid-layered sponge of interest included the lower sponge-like layer (i.e., a first layer) containing AL500 and calcium chloride, and the upper sponge-like layer containing AL10 and calcium chloride (i.e., a second layer). The alginic acid-layered sponge was generally circular with a diameter of 35 mm and a thickness of 1.83±0.13 cm (n=4). The total amount of sodium alginate used in the upper layer and the lower layer was about 2.0 mg/cm$^2$. The ratio (weight ratio) of the sodium alginate used in the upper layer and the lower layer was 1:1. Furthermore, the amount of calcium chloride used was about 1.0 μmol/cm$^2$ in the upper layer and about 1.5 μmol/cm$^2$ in the lower layer.

(5) Measurement of Weight Average Molecular Weight

The weight average molecular weight of the alginic acid used as a production feedstock was measured by GPC-MALS method below.

[Pretreatment Method]
An eluent was added to dissolve a sample, which was filtrated through a 0.45 μm membrane filter to obtain a measurement solution.
[Measurement Conditions (Refractive Index Increment (dn/dc) Determination)]
Differential refractometer: Optilab T-rEX
Measurement wavelength: 658 nm
Measurement temperature: 40° C.
Solvent: 200 mM aqueous sodium nitrate solution
Sample concentration: 0.5-2.5 mg/mL (5 concentrations)
[Measurement Conditions (Absolute Molecular Weight Distribution Determination)]
Columns: TSK gel GMPW-XL×2+G2500PW-XL (7.8 mm I.D.×300 mm×3 columns)
Eluent: 200 mM aqueous sodium nitrate solution
Flow rate: 1.0 mL/min.
Concentration: 0.05%
Detector: RI detector, light scattering detector (MALS)
Column temperature: 40° C.
Injection amount: 200 μL
[Results]
AL10: 55,000
AL500: 280,000

A single-layer sponge containing AL10 and a single-layer sponge containing AL500 prepared according to the procedures of steps (1), (2) and (4) above were subjected to electron beam sterilization, and then dissolved in an EDTA (ethylenediaminetetraacetic acid) solution to respectively measure their molecular weights by GPC-MALS method. The results are shown below.

[Results]

(Where the radiation dose for electron beam sterilization was 20 kGy)

AL10: 36,000
AL500: 75,000

(Where the radiation dose for electron beam sterilization was 40 kGy)

AL 10: 27,000
AL500: 45,000

In Examples 3, 3-2 and 4 described below, the laminated sponges used were those that had been subjected to electron beam sterilization (20 kGy).

In Examples 6 and 7 described below, the laminated sponges used were nonsterile.

Example 1-2

Preparation of Alginic Acid-Layered Sponge (1) Preparation of Sponge

Using the alginic acids listed in [Regents] below, i.e., AL100 or AL500 as a feedstock of the lower layer and AL10 or AL20 as a feedstock of the upper layer, alginic acid-layered sponges were prepared in combinations of AL10 (upper layer)-AL100 (lower layer), AL20 (upper layer)-AL100 (lower layer) and AL20 (upper layer)-AL500 (lower layer), respectively, according to the method described in Example 1.

[Reagents]

AL10: Same as Example 1
AL20: (Lot NO. BL150713-20), endotoxin level 13 EU/g
AL100: (Lot NO. 5G17201), endotoxin level 6 EU/g
AL500: Same as Example 1

(2) Measurement of Weight Average Molecular Weight

Furthermore, weight average molecular weights of AL20 and AL100 among the alginic acids used for sponge preparation were measured by GPC-MALS method according to the method described in Example 1.

[Results]

AL20: 82,000
AL100: 170,000

The molecular weights of a single-layer sponge containing AL20 and a single-layer sponge containing AL100, which were prepared according to the method described in Example 1 were also measured after electron beam sterilization according to the method described in Example 1. The results are shown below.

[Results]

(Where the radiation dose for electron beam sterilization was 20 kGy)

AL20: 46,000
AL100: 63,000

(Where the radiation dose for electron beam sterilization was 40 kGy)

AL20: 33,000
AL100: 40,000

Example 2

Determination of Dissolution Rate of Each Layer of Alginic Acid-Layered Sponge

Laminated sponges that have either fluorescently modified upper layer or lower layer were prepared to determine the dissolution rates. Detail of the procedure will be described below. Here, the alginic acid was labeled by a common method using FTSC (fluorescein-5-thiosemicarbazide) as a fluorescent labeling agent.

The fluorescent-labeled alginic acid was used to prepare a laminated sponge according to the method described in Example 1.

[Materials]

The low-endotoxin sodium alginate was as described in Example 1. A phosphate buffer solution was prepared using sodium dihydrogen phosphate (Wako Pure Chemical Industries, Ltd., 197-09705 (trade name)), potassium dihydrogen phosphate (Wako Pure Chemical Industries, Ltd., 166-04255 (trade name)), sodium chloride (Wako Pure Chemical Industries, Ltd., 191-01665 (trade name)), and potassium chloride (Wako Pure Chemical Industries, Ltd., 166-17945 (trade name)). Ethylenediamine tetraacetic acid sodium (N001) was purchased from Dojindo.

[Instruments Used]

8 mm-diameter biopsy punch (BP-80F (trade name), Kai medical)

96-well black microplate (137101 (trade name), Nunc)

Fluorescent microplate reader (ARVO X3 (trade name), Perkin Elmer)

[Procedure]

First, a fluorescently modified laminated sponge was punched with the 8 mm-diameter biopsy punch (BP-60F (trade name), Kai medical). The resultant was immersed in 10 mL of a 150 mM phosphate buffer solution (pH7.5), and 200 μL each of the immersion solution was collected at regular intervals. The collected solutions were transferred into the 96-well microplate, and the fluorescent intensities were determined with the fluorescent microplate reader to quantify the amounts of the dissolved alginic acid.

[Results]

Figure 2:
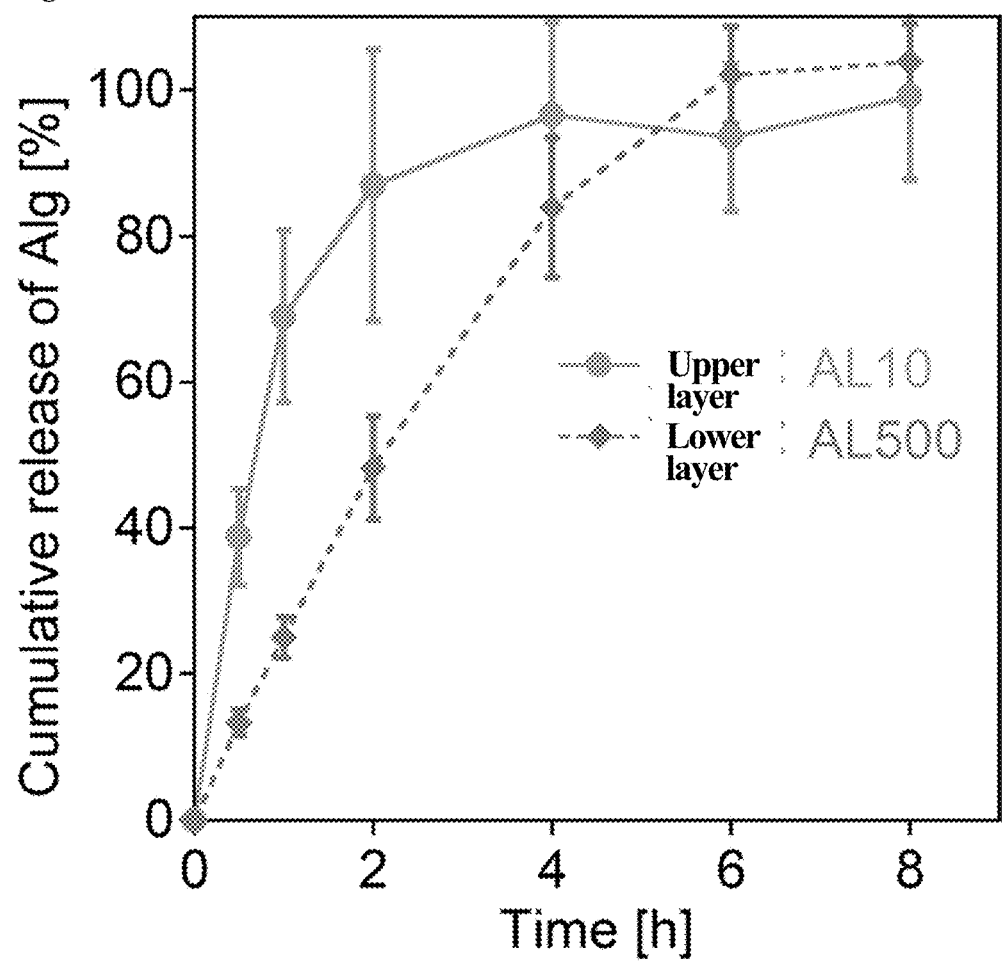
FIG. 2 A diagram showing evaluation of the dissolution rates of the respective layers of the adhesion-preventing material.

The results from determination of the dissolving behavior of each layer of the laminated sponge are shown in FIG. 2. As can be appreciated from FIG. 2, for the lower layer, 25±10 wt % of the monovalent metal salt of alginic acid was eluted within an hour, and 80±10 wt % was eluted within 4 hours. Meanwhile, for the upper layer, 70±10 wt % of the monovalent metal salt of alginic acid was eluted within an hour and 90±10 wt % was eluted within 4 hours. Moreover, the ratio of the elution amount of the monovalent metal salt of alginic acid in the lower layer was 36% (less than 50%) after an hour and 55% (less than 70%) after two hours following the start of the measurement, when taking the elution amount of the monovalent metal salt of alginic acid in the upper layer as a base of 100%.

Thus, the dissolution rate of the upper layer was confirmed to be faster than that of the lower layer. By applying the alginic acid sponge such that the lower layer faces the wound while the upper layer faces the abdominal cavity, the lower layer is considered to remain on the wound and prevent an adhesion of the wound while the upper layer is considered to dissolve relatively faster and suppress de novo adhesions such as adhesions in the whole abdominal cavity that are often formed remote from the wound.

Dissolution rates were similarly determined for the respective laminated sponges produced in Example 1-2 (AL10 (upper layer)-AL100 (lower layer); AL20 (upper layer)-AL100 (lower layer); and AL20 (upper layer)-AL500 (lower layer)). As a result, they showed similar dissolving behavior as that of the laminated sponge produced in Example 1 (AL10 (upper layer)-AL500 (lower layer)).

Example 3

Partially Resected Rat Hepatic Model

Partially resected rat hepatic models were used to evaluate formation of adhesions. A partially resected rat hepatic model is a model that causes serious inflammation and that allows highly reproducible observation of highly intense adhesion formation (Shimizu A et al., (2014) Surg Today. (44): 314-323). Specifically, formation of an adhesion was evaluated as follows.

[Materials]

The low-endotoxin sodium alginates were the same as described in Example 1.

Seprafilm (trade name) was a sheet-like material of a mixture of carboxymethyl cellulose (CMC) and hyaluronic acid, which was obtained from Genzyme GmbH.

Interceed (trade name) was an oxidized regenerated cellulose sheet, which was obtained from Johnson & Johnson.

[Experimental Groups]

Control group (n=8): 3 cm of the margin of the left lateral lobe was measured and dissected, and bleeding was stopped by coagulation (untreated control group).

500-10 laminated sponge group (n=8): The alginic acid sponge produced in Example 1 was applied as an adhesion-preventing material.

Seprafilm group (n=8): 2×3 cm Seprafilm was applied as an adhesion-preventing material.

Interceed group (n=8): 2×3 cm Interceed was applied as an adhesion-preventing material.

[Procedure]

Anesthesia of a rat was performed by abdominal administration of 35 mg/kg of pentobarbital. The weight was measured with an electronic balance. Subsequently, midline abdominal incision was made in the rat. Then, the abdominal wall was pulled up with forceps to cut the abdominal wall. As preparation prior to hepatic resection, the left lateral lobe was pulled out from inside the abdominal cavity, gauze was laid underneath. Thereafter, actual hepatic resection was carried out. Specifically, a ruler was applied to the liver to find out the position for obtaining a 3-cm resected surface, which was marked by cauterizing both ends with a bipolar. A linear cut was made between the marked two points. For the control group, the abdomen was closed immediately thereafter to complete the treatment. For the groups to be applied with the adhesion-preventing material, the adhesion-preventing material was applied after removing the gauze. Subsequently, sutures were made in two steps in the abdominal wall and the skin to close the abdomen. The abdominal wall was sutured using a biodegradable suture while the skin was sutured with a nonabsorbable suture. A week following the abdominal closure, the rat was euthanized by administering about 2 mL of pentobarbital as an excessive dose of anesthesia and the weight was measured using an electronic balance. Thereafter, the abdomen was reopened to evaluate adhesions as follows. After dissecting the spleen from the abdominal cavity, the spleen weight was measured using an electronic balance.

[Evaluation of Adhesions]

The adhesions were evaluated as follows.

(1) Resection Surface

The following evaluations (a) and (b) were performed on the resected liver surface described in [Procedure] above.

(a) Adhesion Grade

The adhesion was evaluated by visual observation. The adhesion of the resected liver surface was scored based on the following scoring.

Scoring of adhesion:

Grade 0: No adhesion is observed

Grade 1: Adhesion that can be separated with gravity (physiological dissection)

Grade 2: Adhesion that can be separated with forceps (blunt dissection)

Grade 3: Adhesion that cannot be separated without scissors or a scalpel (sharp dissection)

(b) Adhesion Extent

The width of the adhesion formed on the 3-cm resected liver surface was measured with a ruler and expressed as a length (unit: mm) (thus, the maximum extent of the resected surface would be 30 mm).

(2) Unresected Surface

The following evaluations (a) and (b) were performed on parts other than the resected liver surface, specifically, liver surface, greater omentum, peritoneal, small intestine, a part directly under the midline wound and the like.

(a) Adhesion Grade

The adhesion was evaluated by visual observation. The adhesion of the part other than the resected liver surface was scored based on the following scoring. The part of the adhesion was not specified, and the maximum adhesion score observed was recorded as the adhesion score of the test animal.

Scoring of Adhesion:

Grade 0: No adhesion is observed

Grade 1: Adhesion that can be separated with gravity (physiological dissection)

Grade 2: Adhesion that can be separated with forceps (blunt dissection)

Grade 3: Adhesion that cannot be separated without scissors or a scalpel (sharp dissection)

(b) Adhesion Extent

The width of the tissue site with an adhesion for the part other than the resected liver surface was measured with a ruler and expressed as lengths (unit: mm). Similar to (2)(a) above, the part of the adhesion was not specified, and the maximum width observed with adhesion formation was recorded as the adhesion extent of the test animal.

[Results]

Figure 3A:
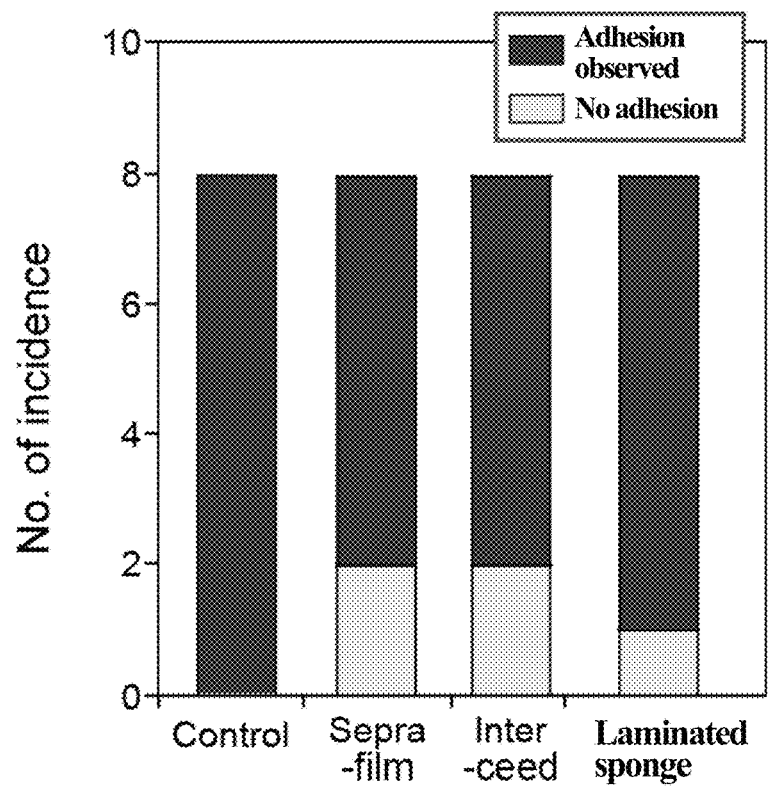
FIGS. 3A-3C Diagrams showing evaluations of adhesion formation in partially resected hepatic models.
Figure 3B:
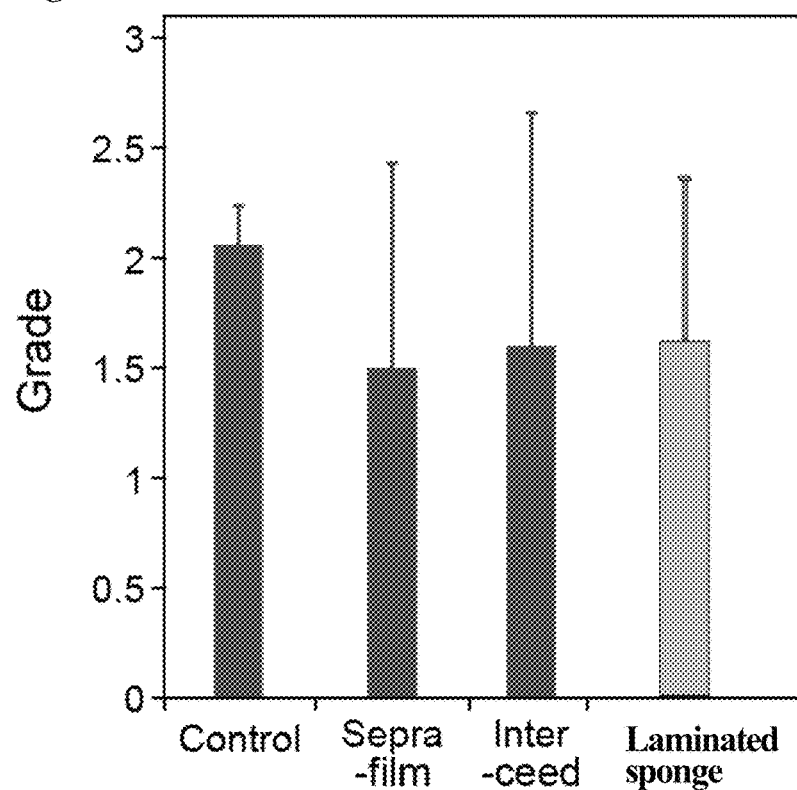
Figure 3C:
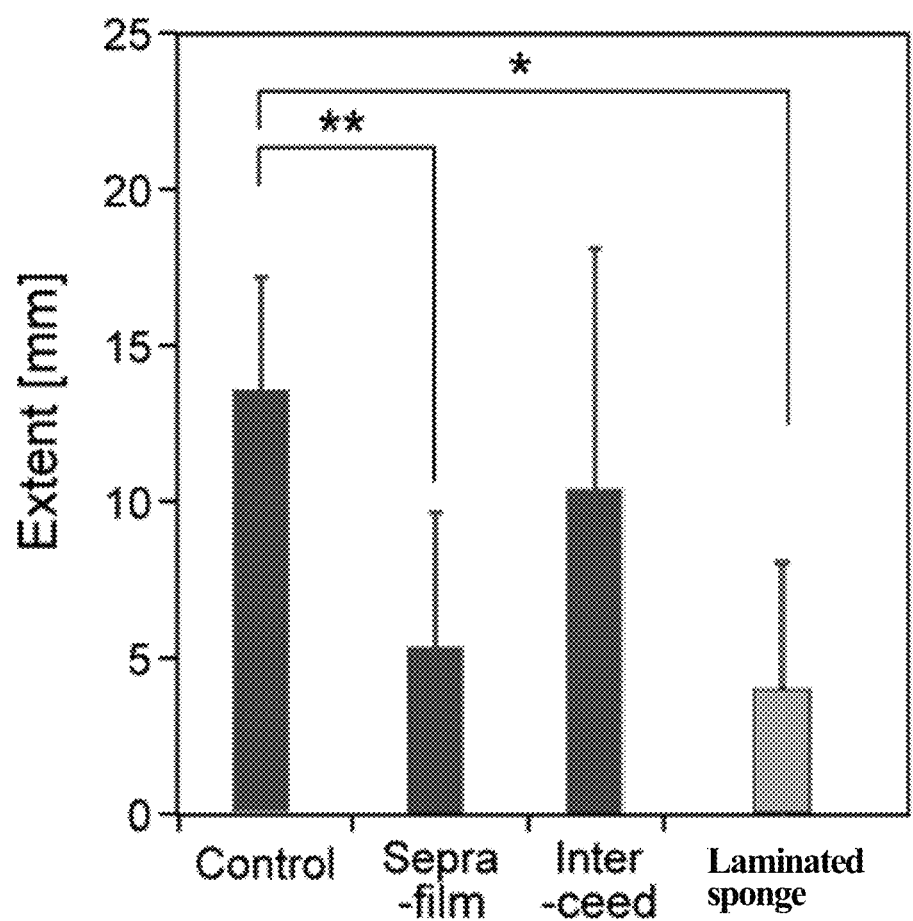
Figure 4A:
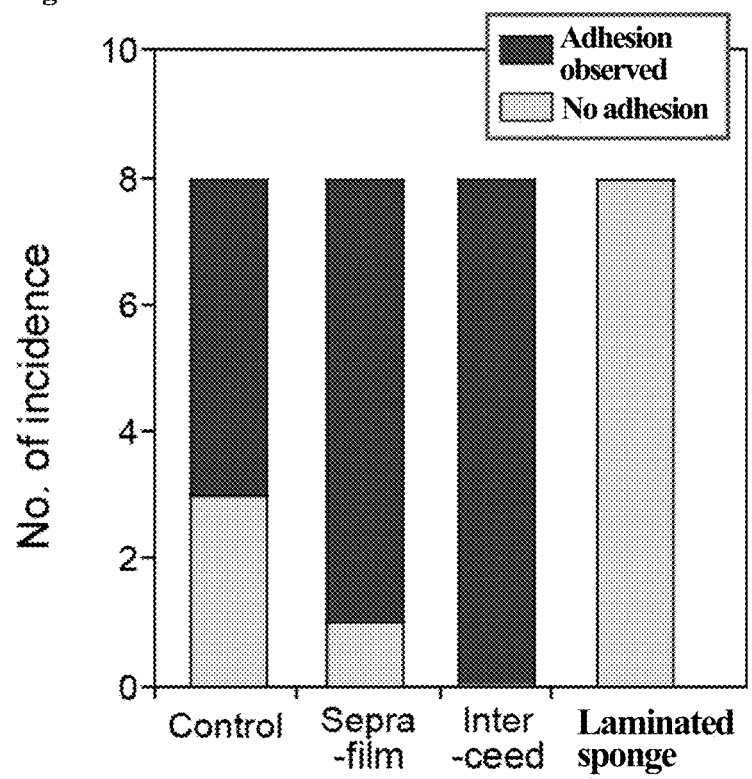
FIGS. 4A-4C Diagrams showing evaluations of adhesion formation in the partially resected hepatic models.
Figure 4B:
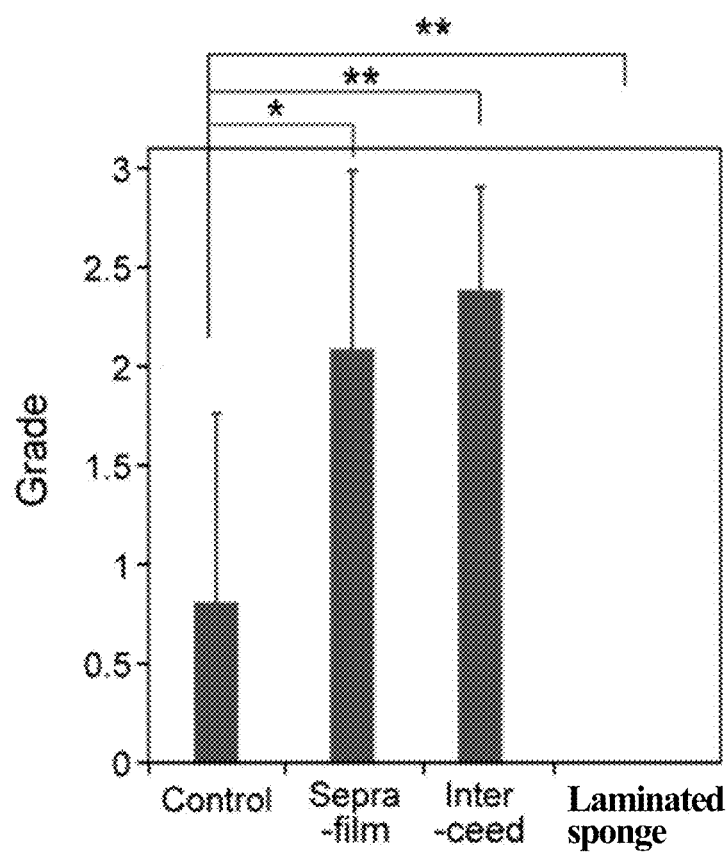
Figure 4C:
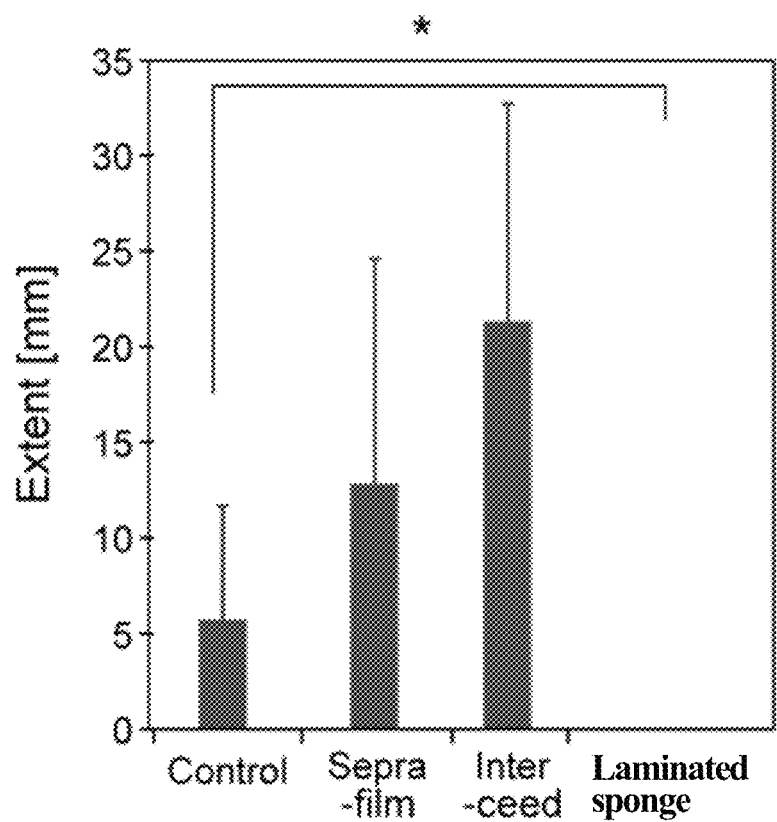

The results from the adhesion evaluations are shown in FIGS. 3A-3C (resected surface) and FIGS. 4A-4C (unresected surface). In addition, the results from the weight measurements and spleen weight measurements are shown in FIGS. 5A-5B.

For each group, adhesions on the resected surfaces were found to be suppressed as compared to the control group (FIGS. 3A-3C).

A remarkable adhesion prevention effect was confirmed on the unresected surface for the 500-10 laminated sponge group (FIGS. 4A-4C). Seprafilm (trade name) and Interceed (trade name) that were used as the positive controls had no adhesion prevention effect, and the adhesions were found to worsen as compared to the control group. Meanwhile, a remarkable adhesion prevention effect was confirmed for the 500-10 laminated sponge group.

Figure 5A:
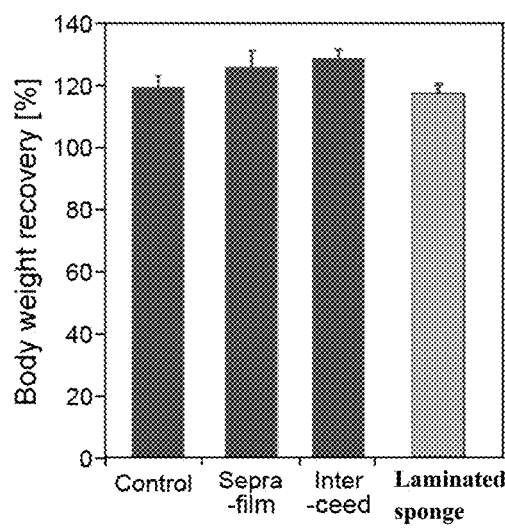
FIGS. 5A-5B Diagrams showing evaluations of change in body weight and spleen weight of the partially resected hepatic models.
Figure 5B:
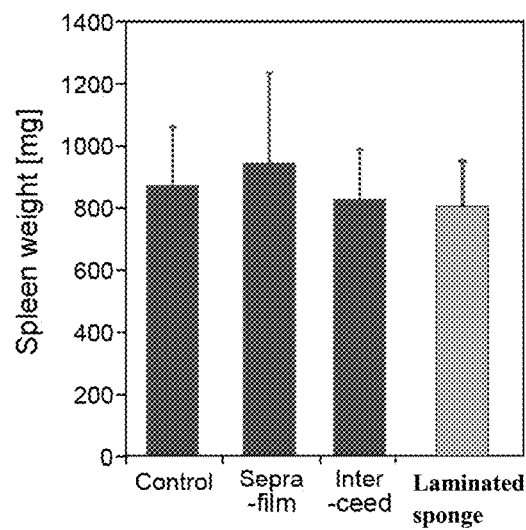

As to the weight and the spleen weight, there was no significant difference among the control group, the Seprafilm group, the Interceed group and the 500-10 laminated sponge group, confirming that the application of the 500-10 laminated sponge had no adverse effect on the living body (FIGS. 5A and 5B).

Herein, unless otherwise specified, the significance tests in the examples were conducted by Student's t-test, except that evaluations of grades were conducted by Mann-Whitney U test.

Example 3-2

Rat Hepatic Model Partially Resected with Pean Clamp

The adhesion grades and the adhesion extents of resected and unresected liver surfaces were evaluated using the same material, experimental groups, procedures and adhesion evaluation methods as Example 3 except that a Pean clamp was used upon liver dissection.

Dissection of the liver using a Pean clamp was carried out specifically as follows. Specifically, the "linear cut between the marked two points" described in [Procedure] of Example 3 was made by crushing liver parenchyma with a Pean clamp, and cauterizing the exposed blood vessel with a bipolar.

[Results]

Figure 6A:
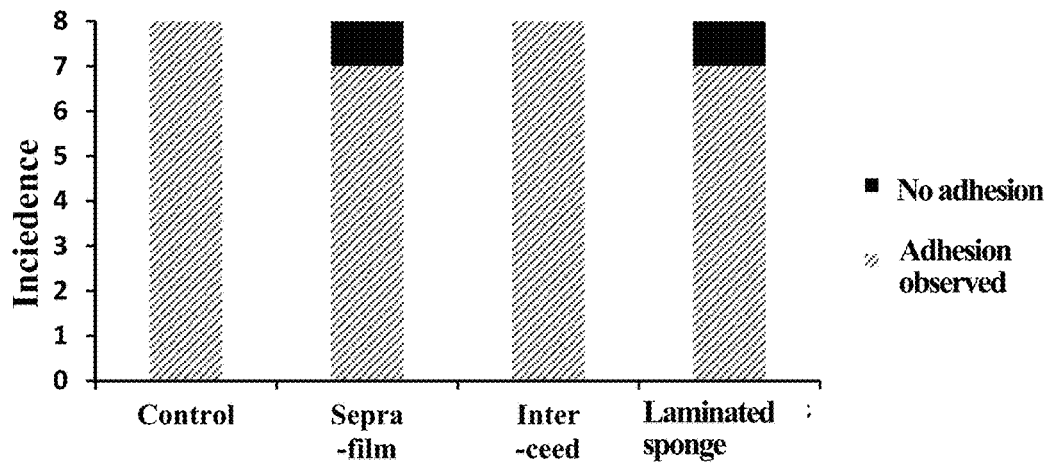
FIGS. 6A-6C Diagrams showing evaluations of adhesion formation in Pean clamp-resected hepatic models.
Figure 6B:
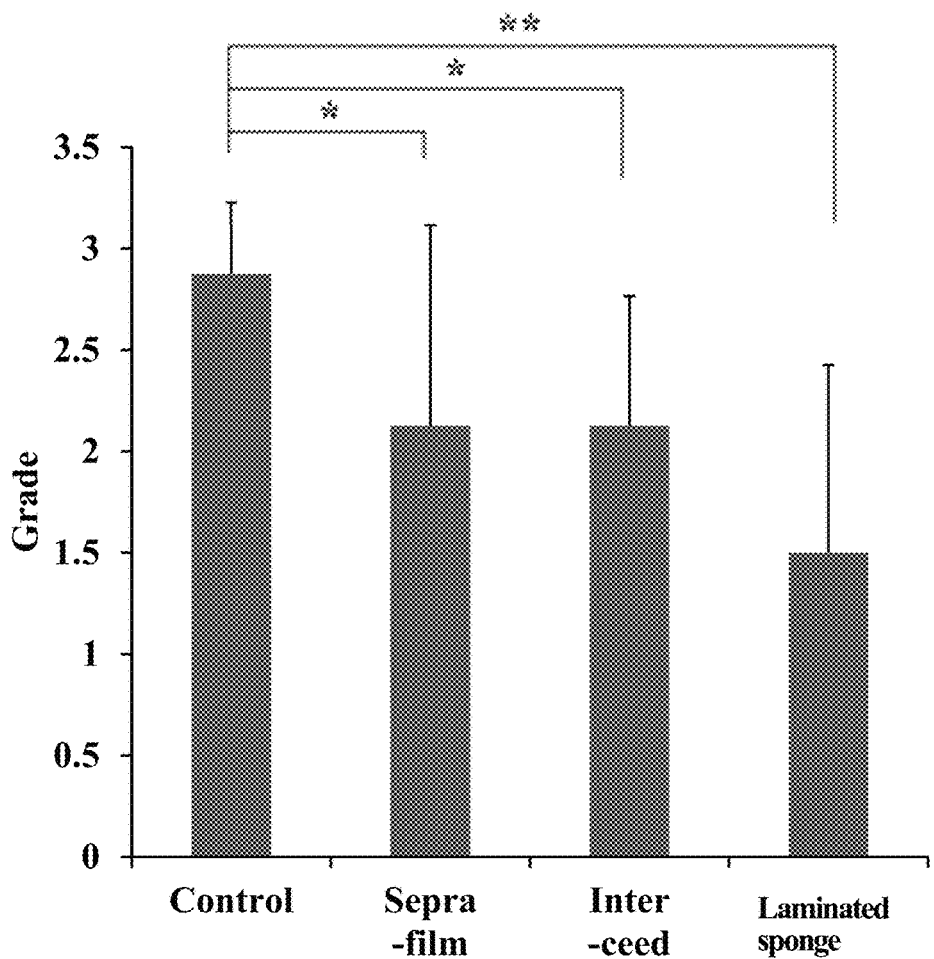
Figure 6C:
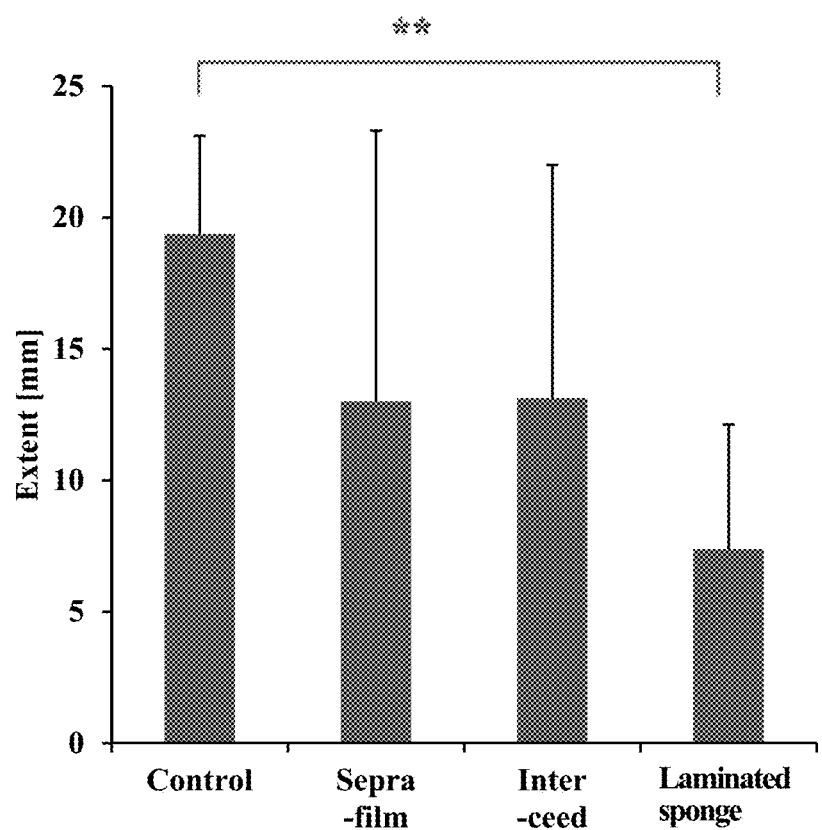
Figure 7A:
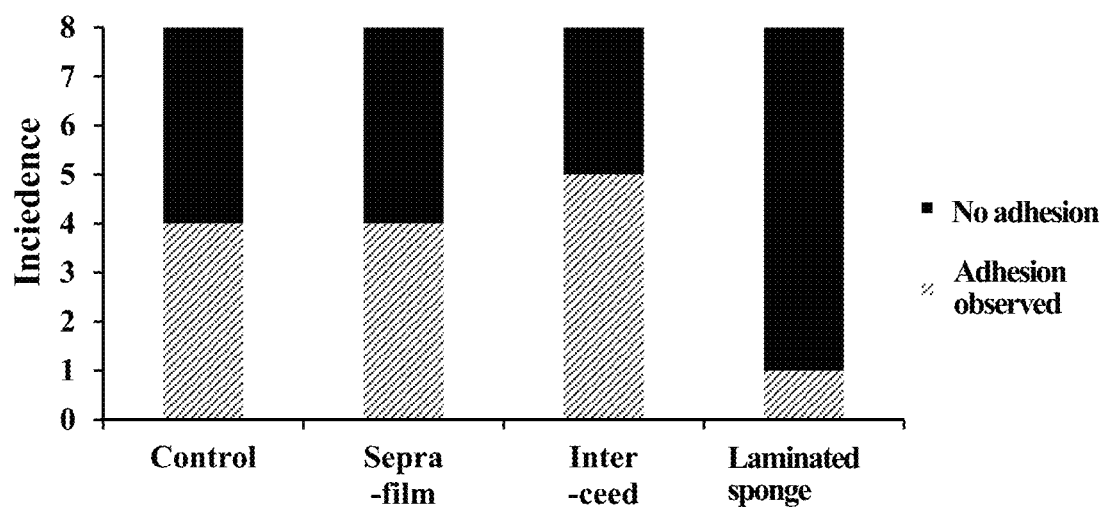
FIGS. 7A-7C Diagrams showing evaluations of adhesion formation in the Pean clamp-resected hepatic models.
Figure 7B:
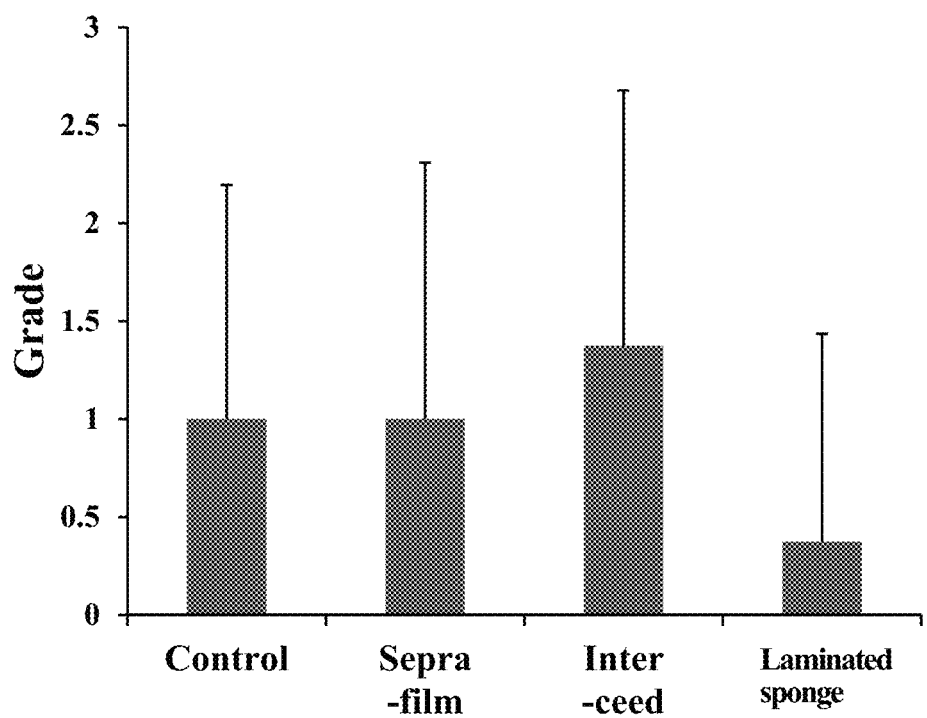
Figure 7C:
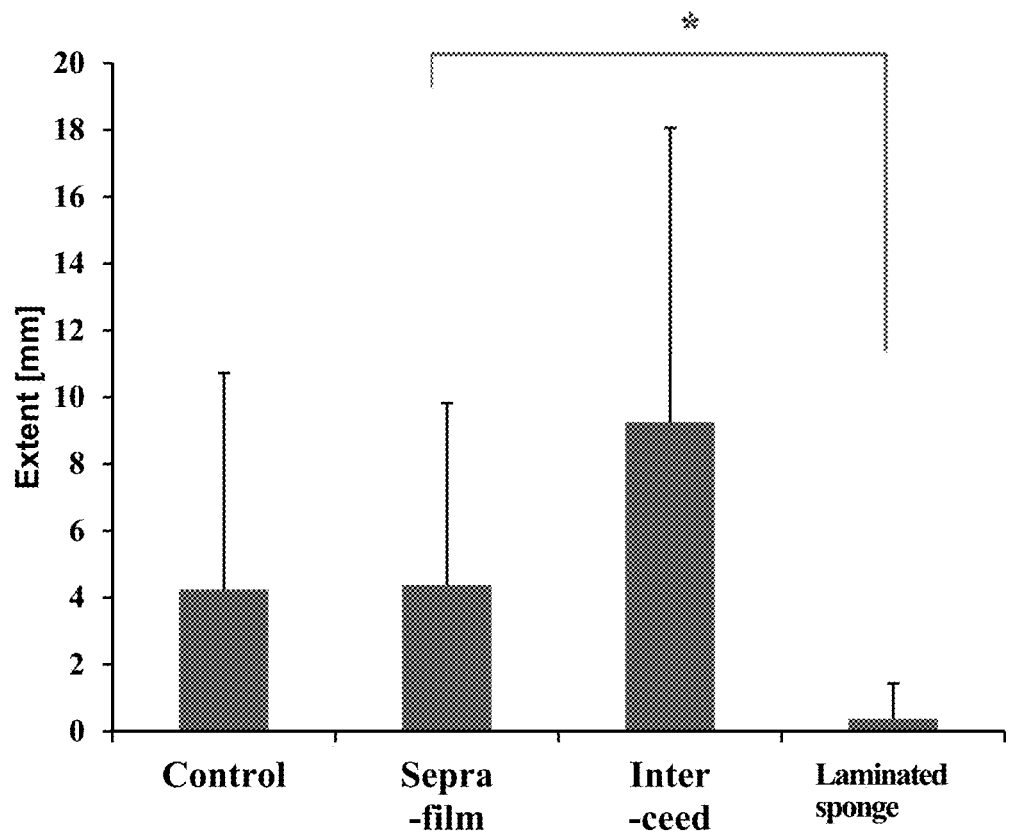

The results from the adhesion evaluations are shown in FIGS. 6A-6C (resected surface) and FIGS. 7A-7C (unresected surface). In addition, the results from the weight measurements and spleen weight measurements are shown in FIGS. 8A-8B.

For each group (n=8), adhesions on the resected surfaces were found to be suppressed as compared to the control group (n=8), where the 500-10 laminated sponge group showed a statistically significant difference from the control group (FIGS. 6A-6C).

A remarkable adhesion prevention effect was confirmed on the unresected surfaces of the 500-10 laminated sponge group (FIGS. 7A-7C). No adhesion prevention effect was observed with Seprafilm (trade name) that was used as the positive control while the adhesion tended to worsen with Interceed (trade name) as compared to the control group. Meanwhile, a remarkable adhesion prevention effect was confirmed for the 500-10 laminated sponge group.

Figure 8A:
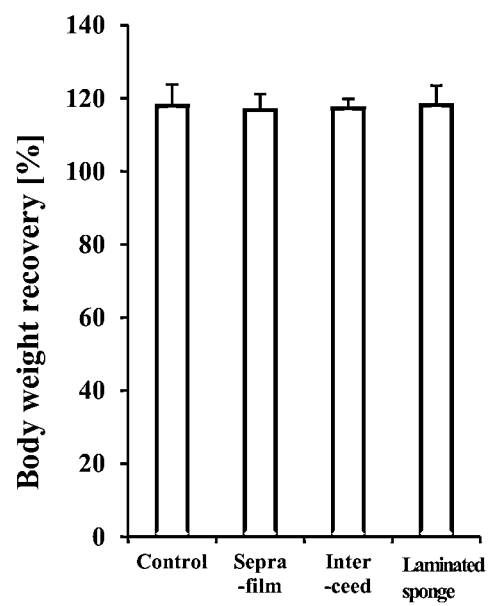
FIGS. 8A-8B Diagrams showing evaluation of change in body weight and spleen weight of the Pean clamp-resected hepatic models.
Figure 8B:
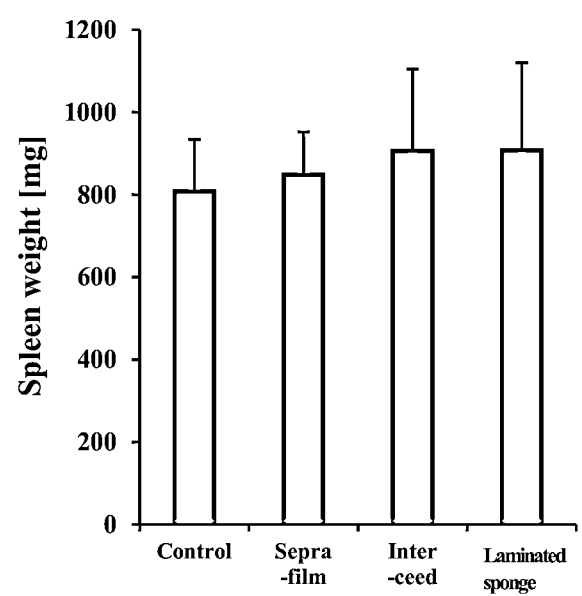

As to the weights and the spleen weights, there was no significant difference among the control group, the Seprafilm group, the Interceed group and the 500-10 laminated sponge group, confirming that the application of the 500-10 laminated sponge had no adverse effect on the living body (FIGS. 8A and 8B).

Example 4

Visualization of Each of Layers of the Alginic Acid-Layered Sponge by Fluorescent Labeling Each layer of the alginic acid-layered sponge was visually examined by fluorescent labeling as follows.

[Materials]

Low-endotoxin sodium alginates were the same as described in Example 1.

[Instruments Used]

Handheld UV lamp (UVGL-58 (trade name), UVP)

[Procedure]

The procedure for resecting a rat liver was the same as described in Example 3. An alginic acid sponge having a first layer or a second layer fluorescently labeled was placed on the resected surface of the prepared liver. In order to facilitate observation of the remaining level of the material, a laminated sponge using an alginic acid for 4.0 mg/cm$^2$ which was greater than Example 1 was prepared and used according to the method of Example 1. Thereafter, the abdomen was closed according to the procedure described in Example 3, and the abdomen was reopened a week later. An ultraviolet lamp was used to irradiate inside the exposed abdominal cavity so as to visualize the distribution of the fluorescent-labeled alginic acid inside the abdominal cavity.

As a result, the AL10 layer was confirmed to be widely distributed over the resected surface and the peritoneal surface. From this, the second layer of the sponge-like laminate was suggested to rapidly melt and spread inside the abdominal cavity owing to the relatively low weight average molecular weight of the monovalent metal salt of alginic acid.

Meanwhile, fluorescence from the AL500 layer was partially observed on the abdominal wall and more significantly observed on the resected surface. From this, the first layer of the sponge-like laminate was suggested to remain on the resected surface and serves as a physical barrier owing to the relatively high weight average molecular weight of the monovalent metal salt of alginic acid.

Example 5

Wrap Test

In order to see the adhesive followability of the alginic acid-layered sponge on a curved surface, a wrap test was conducted as follows.

[Materials]

A low-endotoxin sodium alginate was the same as described in Example 1. Agar (010-08725) was purchased from Wako Pure Chemical Industries, Ltd.

[Procedure]

Agar was dissolved in hot water and then poured and cooled in a columnar mold to give an agarose gel column with a diameter of 20 mm. This was used as a model tubular organ, around which the sponge produced in Example 1 was wrapped to verify the wrapping followability.

As a result, the sponge was confirmed to be capable of being wrapped around the column resembling an intestinal tract owing to flexibility of the alginic acid-layered sponge. This suggested that an adhesion-preventing material comprising a sponge-like laminate can also be used for intestinal anastomosis and the like.

Example 6

Pressing of Sponge and Swelling Test Thereof

Pressing of the alginic acid-layered sponge, a measurement of thickness thereof and swelling test after the pressing were conducted as follows.

[Materials]

The alginic acid-layered sponge (AL10 (upper layer)-AL500 (lower layer)) was the same as described in Example 1.

[Reagents]

Agarose was obtained from Wako Pure Chemical Industries, Ltd. (Product code: 010-08725).

[Procedure]

(1) Pressing and Measurement of Thickness After Pressing (1-1) Manual Pressing

The alginic acid-layered sponge was placed on a flat surface and pressed with the palm via an acrylic ruler such that the whole sponge was uniformly pressed. The thickness of the sponge was measured with an electronic caliper before and after the pressing. The average was calculated (n=4).

(1-2) Pressing with Press Machine

The alginic acid-layered sponge was placed on a press machine (from As One, product name AH-1T). The alginic acid-layered sponge was pressed at a pressure of 10 MPa at room temperature and held for 5 minutes. The thickness of the sponge was measured with an electronic caliper before and after the pressing. The average was calculated (n=4).

(2) Swelling Test

Agar was dissolved in hot water at 2 wt % and cooled to room temperature to prepare an agarose gel. The agarose gel was cut into a 2 cm×2 cm square, which was immersed and wetted with pure water in a glass petri dish.

The alginic acid-layered sponges before and after pressing were cut into a 1 cm×1 cm square and placed on the agarose gel. The thickness of the sponge was calculated by transversely taking pictures at regular intervals so as to confirm the presence of influence of pressing on swelling (unpressed: n=3; pressed: n=3). For the swelling test, the alginic acid-layered sponge that was pressed with the press machine was used.

[Results]

The results from the thickness measurement after pressing are showing in Table 1.

TABLE 1

|  | Unpressed | Manually pressed | Pressed with press machine |
| --- | --- | --- | --- |
| Average thickness (mm) | 1.5 | 0.33 | 0.16 |

The average thickness of the sponges was about 1.5 mm before pressing, about 0.33 mm after manual pressing and about 0.16 mm after pressing with the press machine. The thickness of the pressed sponge did not increase with time and the above-mentioned thickness was maintained.

Figure 9:
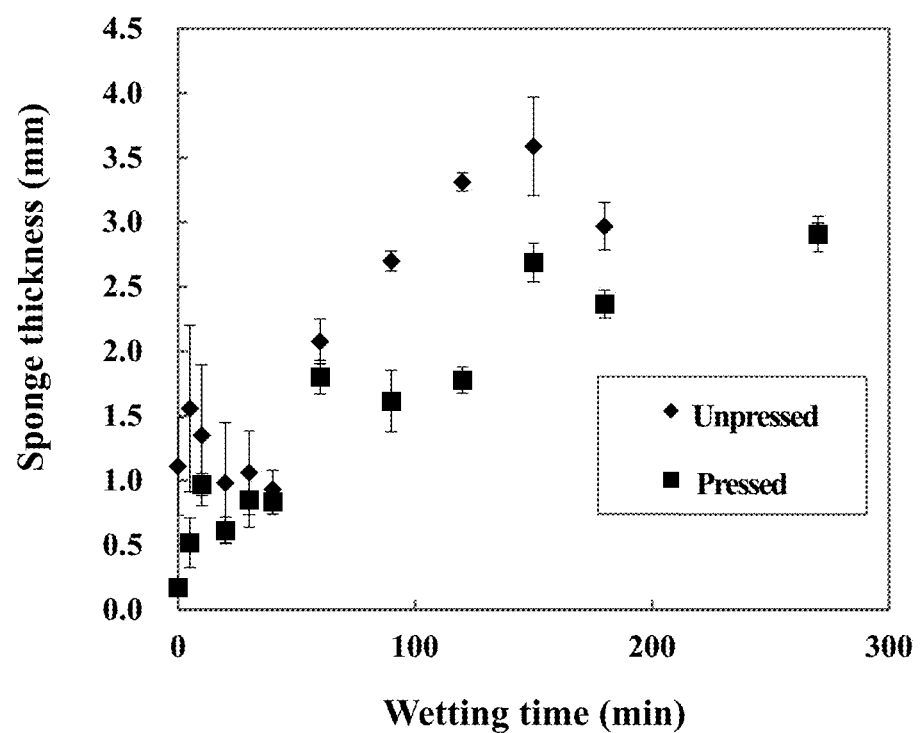
FIG. 9 A diagram showing results from sponge swelling tests before and after pressing.

Changes in the thickness of the sponge with time in the swelling test are shown in FIG. 9. Regarding the results from the swelling test, the pressed alginic acid-layered sponge was confirmed to restore the thickness substantially equal to that of the unpressed alginic acid sponge by water absorption.

This suggested that since the sponge can be made compact by pressing, the sponge can relatively easily be applied as an adhesion-preventing material to an affected area via a trocar or the like upon an endoscopic surgery.

It was also suggested that the pressed sponge applied to the affected area absorbs moisture present in or applied to the affected area to restore the thickness. By restoring the thickness, the laminated sponge can exert its functions.

Example 7

Spraying Test

Vulnerability of the alginic acid-layered sponge and Seprafilm (trade name) upon water absorption were evaluated by the following test.

[Materials]

The alginic acid-layered sponge was the same as that described in Example 1 and Seprafilm (trade name) was the same as that described in Example 3. Moreover, the pressed alginic acid-layered sponge used was pressed with the press machine described in Example 6.

[Procedure]

1 cm×2 cm test pieces were made from the alginic acid-layered sponge and Seprafilm (trade name). A double-sided tape was adhered on one end (1 cm×1 cm) of the test piece, and held at an edge of a test board so that the test piece was fixed with the other end (1 cm×1 cm) sticking out in the air.

Pure water was sprayed five times on each of the test pieces using an atomizer. Video of the course of the test piece bending downward by wetting was taken.

Based on the image analysis of the obtained video, both the height and the angle of the tip of the test piece with respect to the test board were calculated and their changes were plotted with time.

[Results]

Figure 10A:
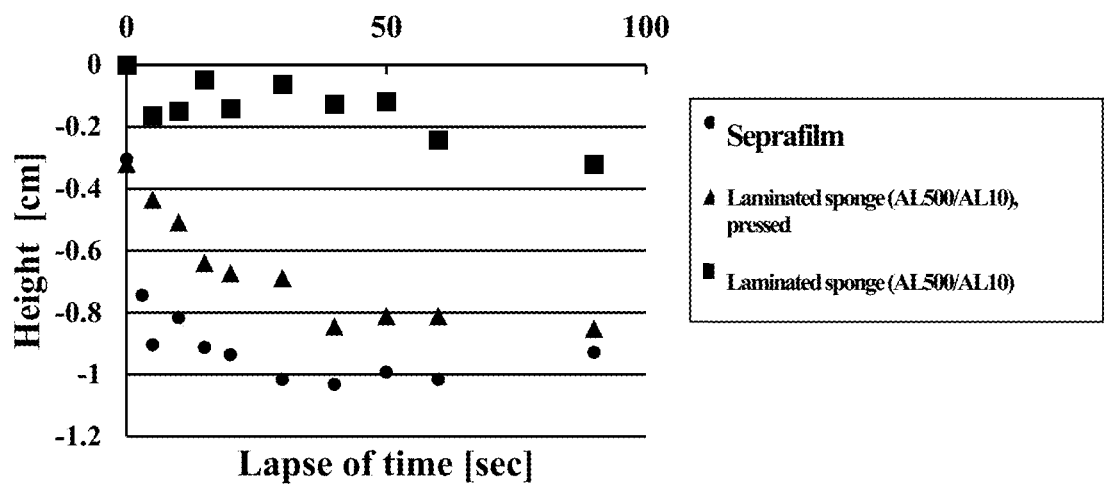
FIGS. 10A-10B Diagrams showing changes in (FIG. 10A) the height and (FIG. 10B) the angle against the test board of the tip of each test piece with time after spraying.
Figure 10B:
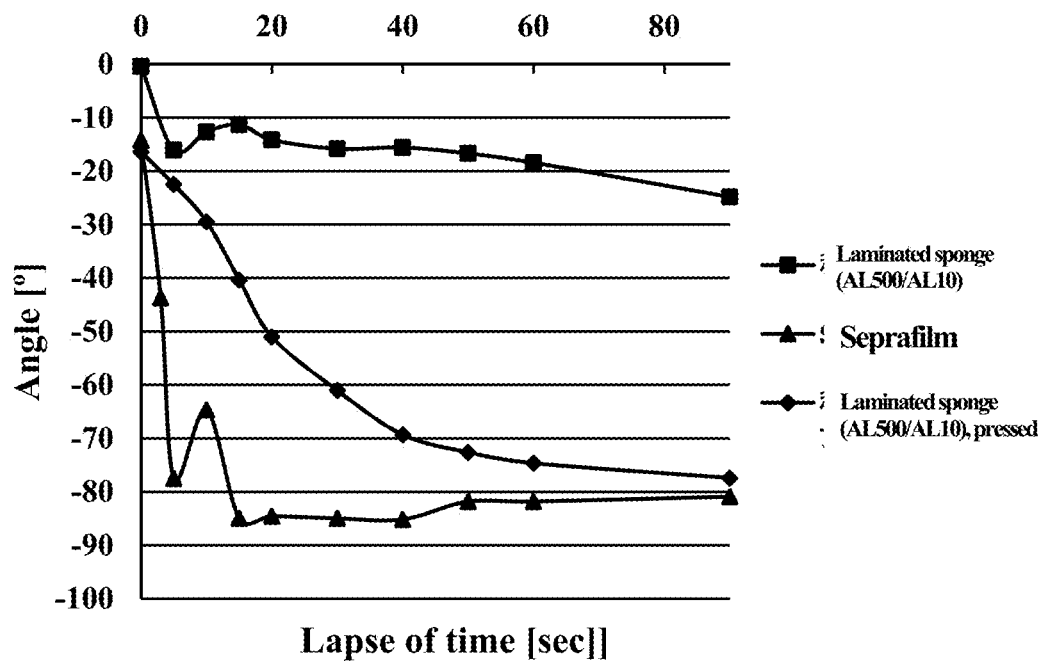

The results are shown in FIGS. 10A-10B.

The decrease in the height of the alginic acid-layered sponge was within 2 mm until 50 seconds following spraying, and about 3 mm after 90 seconds (FIG. 10A). The decrease in the height of the pressed alginic acid-layered sponge was also about 9 mm after 90 seconds following spraying. On the other hand, Seprafilm (trade name) showed a significant decrease in the height immediately after spraying (FIG. 10A). The results for the angle were similar to those for the height (FIG. 10B).

This suggested that the alginic acid-layered sponge can maintain its shape and strength for a while in a wetted state either pressed or unpressed. Therefore, it has advantages such as that it can be reattached to adjust its attached position when applied to an affected area as an adhesion-preventing material, or that it can avoid situation like it cannot be smoothly opened by absorbing moisture in a trocar or the like when the sponge is applied as an adhesion-preventing material to an affected area via a trocar or the like upon an endoscopic surgery. The alginic acid-layered sponge has been confirmed to have a favorable pressure bonding property to an affected area or to a model system thereof in Examples 3, 5 and else.

DESCRIPTION OF REFERENCE NUMERALS

1 Adhesion-preventing material
2 First layer
3 Second layer
4 Sponge-like laminate

The invention claimed is:

1. A method for preventing an adhesion, comprising applying a sterilized biocompatible sponge-like laminate that includes first and second sponge-like layers containing low-endotoxin monovalent metal salts of alginic acid which are at least partially crosslinked with a curing agent, wherein a weight average molecular weight of the monovalent metal salt of alginic acid in the first layer is 10,000-2,000,000, a weight average molecular weight of the monovalent metal salt of alginic acid in the second layer is 1,000-1,000,000, the weight average molecular weights are measured by GPC-MALS method following a decrosslinking treatment, and the weight average molecular weight of the monovalent metal salt of alginic acid in the first layer is higher than the weight average molecular weight of the monovalent metal salt of alginic acid in the second layer, to a subject in need of adhesion prevention.

2. The method according to claim 1, wherein either one of the first layer and the second layer comprises a curing agent.

3. The method according to claim 1, wherein each of the first layer and the second layer comprises a curing agent.

4. The method according to claim 1, wherein the total amount of the low-endotoxin monovalent metal salts of alginic acid used in the first layer and the second layer is in a range of 0.1 mg/cm$^2$-3 mg/cm$^2$.

5. The method according to claim 1, wherein the endotoxin content of the monovalent metal salts of alginic acid in the first layer and the second layer is 500 EU/g or less.

6. The method according to claim 1, wherein the monovalent metal salt of alginic acid in each of the first layer and the second layer are is selected from the group consisting of sodium alginate and potassium alginate.

7. The method according to claim 1, wherein the curing agent in each of the first layer and the second layer is at least one metal ionic compound selected from the group consisting of $CaCl_2$, $CaSO_4$, $ZnCl_2$, $SrCl_2$, $FeCl_3$ and $BaCl_2$.

8. The method according to claim 1, wherein the sponge-like laminate is pressed.

9. The method according to claim 1, wherein the sponge-like laminate is mixed or impregnated with a drug.

* * * * *